(12) United States Patent
Gazit et al.

(10) Patent No.: US 7,504,099 B2
(45) Date of Patent: Mar. 17, 2009

(54) METHODS OF INDUCING OR ENHANCING CONNECTIVE TISSUE REPAIR

(75) Inventors: Dan Gazit, Jerusalem (IL); Gadi Pelled, Rishon Leziyon (IL); Gadi Turgeman, Jerusalem (IL); Andrea Hoffmann, Hannover (DE); Peter Eberle, Braunschweig (DE); Gerhard Gross, Braunschweig (DE)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 184 days.

(21) Appl. No.: 10/330,674

(22) Filed: Dec. 30, 2002

(65) Prior Publication Data

US 2003/0219423 A1    Nov. 27, 2003

Related U.S. Application Data

(63) Continuation-in-part of application No. 10/328,168, filed on Dec. 26, 2002.

(60) Provisional application No. 60/342,375, filed on Dec. 27, 2001.

(51) Int. Cl.
*A61K 48/00* (2006.01)
*A01N 63/00* (2006.01)
*A01N 43/04* (2006.01)

(52) U.S. Cl. .................... 424/93.21; 435/455; 435/372; 536/23.5

(58) Field of Classification Search ........................ None
See application file for complete search history.

(56) References Cited

OTHER PUBLICATIONS

Gafni et al. Stem cells as vehicles for orthopedic gene therapy. Gene therapy 11:417-426, 2004.*
Trippel et al. Gene-based approaches for the repair of articular cartilage. Gene therapy 11:351-359, 2004.*
Moustakas et al. Smad regulation in TGF-beta signal transduction. J. Cell Sci. 114:4359-4369, 2001.*
Itoh et al. Signaling of transforming growth factor-beta family members through Smad proteins. Eur. J. Biochem. 267:6954-6967, 2000.*
Ju et al. The bone morphogenetic protein 2 signaling mediator Smad1 participates predominantly in osteogenic and not in chondrogenic differntiation in mesenchymal progenitors C3H10T1/2. J. Bone and Mineral Res. 15:1889-1899, 2000.*
Hoffmann et al. Neotendon formation induced by manipulation of the Smad8 signalling pathway in mesenchymal stem cells. J. Clin. Invest. 116:940-952, 2006.*

* cited by examiner

*Primary Examiner*—Quang Nguyen

(57) ABSTRACT

This invention provides method for repairing, regenerating, treating, or inducing the repair of an injury, a defect or a condition of a connective tissue of a subject. This invention provides a method of regenerating, enhancing, inducing repair and/or development of connective tissue as a result of a defect, injury or condition of the connective tissue of a subject comprising the step of inserting an engineered cell which comprises a nucleic acid encoding a SMAD protein or variant thereof, so as to induce regeneration, repair and/or development of the connective tissue. This invention further provides methods of ex-vivo implantation of engineered cells into an injury, defect or condition of the connective tissue. This invention also provides a nucleic acid encoding a SMAD 8 protein variant, cells comprising such SMAD 8 variant, include mesenchymal stem cells, progenitor cells or cells derived from a connective tissue. Lastly, this invention provides SMAD 8 protein variant.

7 Claims, 28 Drawing Sheets rat Smad8

BamHI  FLAG-tag  Smad8

```
ggatccgactacaaggacgacgatgacaagcacccagcaccccatcagctccctcttcaccag          80
ccccgcagtgaagaggctgctggctggagcaggaggatgaagaggagaagtgggcagaaggcagtggactctttgg
tgaagaagttaaagaaaagaaaggcgccatgaactgatgaactgcgctgagctgccagctagcaagtgc         240
gttaccattccacgctccctgatgacgcctccagtgtcccacccgaaggcgctgccatgtcatctactgccgcgt
gtggcgctgccagatctgcaatccatcatgagctgaagctgaagtgccctgactgtgccgtttccgttctaagcaga          400
aggagtctgcatcaacccattaccgcagagtggagacccagttctgctgcgtgctgtaccaagacacagc
gagtacaccctcagctcagcctcctggccaagttccgaagtgcctcgcagcgaacctcatgccgcacaacgc         560
cacctacgctccccgcctctctgcagcagtcttccagacaactcaacactcagacttccggccagtt
gcccccaccagctaccgcagtccccgggagtgcttccgtgcctactcacagacgccctctatcagacttccggcatc        720
tgctacgaagcctgcactgtagatgatgaagacagcagacacccctccataacaggaataacaacaggtctcggagagcatc
ctccggagtgtgctcatagatgatagacacagcagacatctctttgtccagaccggaactgcaacctgggaactgcaactgggcagcaaaatg         880
taaacagaaattgacagggatagaaaacaccaaggcactgatctttgtccagaccggaactgcaactcttcgccagacacgcttccagcacccggccac
tacgcggagtgctgaagtgccgagcagcagtccccagtggctgcagctccaaggtcttcaacaaccagctcttcgcccagtcagtgc        1040
tgtctgcaaatcccagtggctgtcttatgaactgacgaagatgtgcacgattcggatggagctttgtgaaggctgggagccgag
accaggcttgaagttcatgcaaaagcacccgtgaactgcaccccctgctgattgagattcatctttcatgaccactgcagtgttgacaaggt        1200
tatcatcgcaggatgtggctccccaccaaacacccactattctttcagtgtcttaagtctcatgtgctcagctgcattccagtcgac         1359
```
Sal I Smad8

FIG.1A rat SMAD8

FLAG-tag → SMAD8 

HPSTPISSLFSFTSPAVKRLLGWKQGDEEEKWAEKAVDSLVKKLKKKGAMDELERALSCPGQPSKCVTIP 80
RSLDGRLQVSHRKGLPHVIYCRVWRWPDLQSHHELKPLECCEFPFGSKQKEVCINPYHYRRVETPVLPPVLPRHSEYNP
QLSLLAKFRSASLHSEPLMPHNATYPDSFQQSLGPAPPSSPGHVFPQSPCPTSYPQSPGSPSESDSPYQHSDERPVCYEE 240
PLHWCSVAYYELNNRVGETFQASSRSVLIDGFTDPSNNRNRFCLGLLSNVNRNSTIENTRRHIGKGVHLYYVGGEVYAEC
VSDSSIFVQSRNCNYQHGFHPATVCKIPSGCSLKVENNQLFAQLLAQSVHHGFEVVYELTKMCTIRMSFVKGWGAEYHRQ 400
DVTSTPCWIEIHLHGPLQWLDKVLTQMGSPHNPISSVS rat SMAD8 L+MH2

FLAG-tag → SMAD8 L+MH2 

EYNPQLSLLAKFRSASLHSEPLMPHNATYPDSFQQSLGPAPPSSPGHVFPQSPCPTSYPQSPGSPSESDSP 80
YQHSDFRPVCYEEPLHWCSVAYYELNNRVGETFQASSRSVLIDGFTDPSMNRNRFCLGLLSNVNRNSTIENTRRHIGKGV
HLYYVGGEVYAECVSDSSIFVQSRNCNYQHGFHPATVCKIPSGCSLKVENNQLFAQLLAQSVHHGFEVVYELTKMCTIRM 240
SFVKGWGAEYHRQDVTSTPCWIEIHLHGPLQWLDKVLTQMGSPHNPISSVS

Blast of Human sequence against mouse sequence:

```
>gi|26024201|ref|NM_019483.2|  Mus musculus MAD homolog 9 (Drosophila) (Madh9),
mRNA
         Length = 1293

Score =  706 bits (356), Expect = 0.0
 Identities = ...
 Gaps = 6/683 (0%)
 Strand = Plus / Plus Query: 751  ccagctaccctcactcccaggaagtccttctgagccagagagtccctatcaacactcag 810
            ||||||||| ||||||||||||||||||||| |||||| |||||||||||||||||||
Sbjct: 614  ccagctacccgcactccccggaagtcctc------agacagtccctatcaacactcag 667

Query: 811  actttcgaccagttgtgttacgagagcccagcactggtgctcggtcgcctactatgaac 870
            |||| ||||||||| |||||| |||||||||||||||||||| || ||||||| ||||
Sbjct: 668  acttccggccagttgctacgagagaacccagcactggtgttctgttgccttactacgaac 727

Query: 871  tgaacaaccgagttgggagacattccaggcttcctccccgaagtgtgctcatagatgggt 930
            |||||||| || || |||||||| ||||||||||| |||||||||||||| |||| | |
Sbjct: 728  taaacaaccgggtcggagagacttccaggcgtcctccgcgagcgtgctcatagacggct 787

Query: 931  tcaccgacccttcaaataacaggaacagagatctgtcttggacttcttctaatgtaaaca 990
            ||||| |||| ||||| ||||| |||||||| ||||||||| || |||| ||||||||||
```

|       |      |
|-------|------|
| FIG. 3C | i    |
| FIG. 3C | ii   |
| FIG. 3C | iii  |
| FIG. 3C | iv   |
| FIG. 3C | v    |
| FIG. 3C | vi   |
| FIG. 3C | vii  |
| FIG. 3C | viii |
| FIG. 3C | ix   |
| FIG. 3C | x    |
| FIG. 3C |      |

FIG. 3C i

```
Sbjct:  788  tcaccgacccttccaataacaggaataggttttgccttggcttctctcaaatgtaaaca  847
             ||||||||||||||||||||||||||||| ||||||||||||||||||||||||||||||
Query:  991  gaaactcaacgatagaaaataccaggagacatataggaaagggtgtgcacttgtactacg 1050
             |||||  |||||| |||||||||||||| |||||||||||||||||||| ||||||||||
Sbjct:  848  gaaactcgaccatagaaaacaccaggaggcacattgaaagggtgtgcatttgtactacg   907

Query: 1051  tcggggagaggtgtatgccgagtgcgtgagtgacagcagcatctttgtgcagagccga   1110
             | ||||| ||||||||||||| |||||||||||||||||||||||||||||| |||||
Sbjct:  908  ttggggcgaggtgtatgccggagtgcgtgagcgacagcagcatcttgtccagagccgga   967

Query: 1111  actgcaactatcaacacggcttccacccagctaccgtctgcaagatcccagcggctgca  1170
             ||||||||| ||  |||| |||||||||||| ||||| ||||||||||||||||||||
Sbjct:  968  actgcaactaccacacgcgcttccacccagcgtctgcaagatcccagcggctgca     1027

Query: 1171  gcctcaagtctcttcaacaaccagctcttcgctcagctcctgccagtcagtcaccacg   1230
             |||||||||||||| |||||| |||||||| ||||| || ||||||||||||||||||
Sbjct: 1028  gcctcaaggtctcttcaacaaccagctcttcgcccagctgctcgccagtcgtcaccacg  1087

Query: 1231  gctttgaagtcgtgtatgaactgaccaagatgtgtactatccggatgagttttgttaagg 1290
             |||||||||| ||||| |||||| ||||||||| ||| |||||||| |||||||| |||
Sbjct: 1088  gctttgaagtggtgtatgagctgacgaagatgtgacgattcgacgtttgtgaagg     1147

Query: 1291  gttggggtgctgagtatcatcgccaggatgtcaccagcaccccctgctgattgagattc  1350
```

FIG. 3C ii

```
Sbjct: 1148  gctggggagcagagtatcatcgccaggatgtcacgagcacccctgctggatcgagatcc  1207
             ||||||  |||  ||||||||||||||||||||||| ||||||||||||||||||||||

Query: 1351  atcttcatgggccactgcagtgctggacaaagttctgactcagatggctctccacata   1410
             ||||||||| || ||||||||||||||  |||||  ||  ||||||||||||| ||||
Sbjct: 1208  atcttcatgaccgctgcagtggttggataaggtgctcactcagatgggctccccacaca 1267

Query: 1411  acccattctcagtgtcttaa  1433
             |||  | |||||||||||||
Sbjct: 1268  acctatctcttcagtgtcttaa  1290

Score = 551 bits (278), Expect = e-153
 Strand = Plus / Plus

Query: 140  tatgcactccaccaccccatcagctccctctccttcaccagccccgcagtgaagag  199
            |||||| ||| |||  ||||||||||||||||||||||||||||||||||||||||
Sbjct: 3    tatgcacccagcaccccatcagctccctctccttcaccagcccgcagtgaagcg   62

Query: 200  actgctaggctggaagcaaggagatgaagaggaaaagtgggcagagaaggcagtggactc  259
            ||| ||||||||||||||||| ||  ||||||||| ||||||||||||| |||||||||
Sbjct: 63   gctgctgggctggaagcaggagatgaagaggaagaagtgggcagagaaggcggtggactc  122
```

FIG. 3C iii

```
Query:  260  tctagtgaagaagttaaagaagaagaaaagggagccatggacgagctggagagggctctcag  319
             |  |||||||||||||||||| || || |||||||||| || || ||||| ||||| || ||
Sbjct:  123  tttggtgaagaagttaaagaagaagaaaagggcgccatggatgaactggagagggcgctgag  182

Query:  320  ctgcccggggcagcccagcaaatgcgtcacgattcccgctccctggacgggcggctgca  379
             ||||| ||| |||||||||||| ||||||||| || ||||| || ||||| || ||
Sbjct:  183  ctgcccggtcagcctagcaagtgtgtcaccatccacacggtccctcgatggacgcctcca  242

Query:  380  ggtgtcccacacgcaagggcctgccccatgtgatttactgtcgcgtgtggcgctggccgga  439
             ||||||||||| |||||||||||| |||| ||||  ||||| |||| || ||||||| ||
Sbjct:  243  ggtgtcccaccgaaagggctgcccacgtcatctactgccgcgtgtggcgctggccaga  302

Query:  440  tctgcagtcccaccacgagctgaagccgctggagtgctgtgagttccatttggctccaa  499
             || ||||| ||| ||| |||||||| |||||||| ||| ||||| ||| ||||||||||
Sbjct:  303  cctgcagtcccatcatgagctgaagccgctggagtgctgtgagttcccgttcggctccaa  362

Query:  500  gcagaaagaagtgtgcattaaccctaccactaccgccgggtggagactccagtactgcc  559
             |||| || ||| ||||||| ||||| || || ||||| ||||||| |||||| ||||
Sbjct:  363  gcagaagaggagtctgcatcaaccatatccgagagtggagacccagttctgcc  422

Query:  560  tcctgtgctcgtgccaagacacagtgaatataaccccagctcagcctcctggccaagtt  619
             || ||||| ||||| |||||||| |||||| ||| |||||||| |||||||||||||||
Sbjct:  423  tccagtgctggtaccaagacacagcgagtacaaccctcagctcagcctcctggccaagtt  482
```

FIG. 3C iv

```
Query:  620  ccgcagcgcctccctgcacagtgagccactcatgccacacaacgccacctatcctgactc  679
             |||  ||   |||||  ||||| ||| |||||||| || ||||||| ||||| ||||||
Sbjct:  483  ccgaagtgcctcgctgcacagcgaaccctcatgccgcacaacgccacctaccctgactc  542

Query:  680  tttccagcag  689
             ||||||||||
Sbjct:  543  tttccagcag  552
```

Blast of Human sequence against rat sequence:

gi|20302033|ref|NM_138872.1|  Rattus norvegicus MAD homolog 9 (Drosophila)
(Madh9), mRNA
       Length = 1611

Score = 579 bits (292), Expect = e-162
Strand = Plus / Plus

```
Query:  134  gcctcttatgcactccaccaccccatcagctccctcttctccttcaccagcccgcagt  193
             |||| || ||||| ||||| ||||||||||||||||| ||||||| |||||||||||
Sbjct:  146  gcctcctatgcaccccagcaccccatcagctccctcttctccttcaccagcccgcagt  205
```

FIG. 3C v

```
Query:  194  gaagagactgctaggctgtggaagcaaggagagtgaagagaaagtgggcagagaaggcagt  253
             |||||  ||||||| ||| ||||||||||||||||||| |||||||| |||||||||||||
Sbjct:  206  gaagaggctgctgctgggctgggcaaggagagtgaagagagaagtgggcagagaaggcagt  265

Query:  254  ggactctctagtgaagaagttaaagaagaagggagccatggacgagctggagagggc     313
             ||||| ||| |||||||||||||||||||| ||||||||||||| |||||||| |||
Sbjct:  266  ggactctttggtgaagaagttaaagaagaagaaagcgccatggatgaactggagaggggc  325

Query:  314  tctcagctgccgggcagcccagcaaatgcgtcacgattcccgctccctggacgggcg      373
             | ||||||||| || ||||||||||| |||||||||||||| ||||||||| |||
Sbjct:  326  gctgagctgccgcgcagcctagcaagtgcgttaccagctccacgctccctgatgatgacg  385

Query:  374  gctgcaggtgtcccacgcaagggcctgccccatgtgatttactgtcgcgtgtggcgctg   433
             || |||||||||||| ||||||  ||||| ||||| ||| |||||||||||||||||||
Sbjct:  386  cctccaggtgtcccacgcaagggggctgccccatgtcatctactgccgcgtgtggcgctg  445

Query:  434  gccggatctgcagtcccaccacgagctgaagccgctggagtgctgtgagttcccatttgg  493
             |||||||||||| |||| || || |||| ||| |||| ||||| |||||||||| ||||
Sbjct:  446  gccagatctgcaatcccatcatgagctgaagccttgaagctgcgagttcccgttttgg   505

Query:  494  ctccaagcagaagaagtgtgcattaaccctaccactacgccggtggagactccagt     553
             || ||| |||| |||  || |||| |||| ||||||| ||| ||||| ||||||||
Sbjct:  506  ctctaagcagaagaggtctgcatcaaccatccacctaccattaccgcagagtggagacccagt  565
```

FIG. 3C vi

```
Query:  554  actgcctcctgtgctcgtgccaagacacagtgaatataaccccagctcagcctcctggc  613
             ||||||||  ||||| ||||||||||||||||  ||| || |  ||||||| |||||||
Sbjct:  566  tctgcctccagtgtgctgtgccaagacacagcgagtacaaccctcagctcagcctctggc  625

Query:  614  caagttccgcagcgcctccctgcacagtgagccactcatgccacacaacgccacctatcc  673
             ||||||||| |  |||||||| |  || ||  |||| || ||  |  |||  |||| ||
Sbjct:  626  caagttccgaagtgcctcgctgcacagcgaaccgctcatgccgcacaacgccacctaccc  685

Query:  674  tgactctttccagcag  689
             |||||||||||||||
Sbjct:  686  tgactctttccagcag  701
```

Score = 521 bits (263), Expect = e-144 
Strand = Plus / Plus

```
Query:  751  ccagctaccctcactcccccaggaagtcctctgagccagagagtccctatcaacactcag  810
             |||||||| |||| ||  |||| ||||||| | ||||| |||||  ||||||||||||||
Sbjct:  763  ccagctacccgcagtccccccgagaagtcctgtcgagtcagacagtcctatcaacactcag  822
```

FIG. 3C vii

```
Query:  811   actttcgaccagtttgttacgaggagcccagcactggtgctcggtcgcctactatgaac  870
              ||||  ||  ||||||||||  ||||||||  ||||||||| ||  ||||||||||||
Sbjct:  823   acttccggccagtttgctacgaggagccctgcactggtgctctgttgcctactacgaac  882

Query:  871   tgaacaaccgagttggggagacattccaggcttcctcccgaagtgtgctcatagatgggt  930
              ||||||||| |||  |||||| | |||||| |||||||||||||||||||||||||  |
Sbjct:  883   tgaacaaccgggtcggagagacttccaggcatcctcccgagtgtgctcatagatggct  942

Query:  931   tcaccgacccttcaaataacaggaacagattctgtctttgacttctttctaatgtaaaca  990
              ||| | ||||| |||||||||||| ||||| ||||||| ||||||||| ||||||||||
Sbjct:  943   tcacagaccctccaataacaggaatagttctgtcttggcttcttcaaatgtaaaca  1002

Query:  991   gaaactcaacgatagaaaataccaggagacatataggaaagggtgtgcacttgtactacg  1050
              |||| |||||||||||||||||||||||| ||||||||||||||||||||||||||||
Sbjct:  1003  gaaattcgacgatagaaaataccaggagacattgaaagggtgtgcatttgtactacg  1062

Query:  1051  tcggggagaggtgtatgccgagtgcgtgagtgacagcagcatctttgtgcagagccgga  1110
              | ||||| ||||||| ||| ||||||| |||||||||||||||||||||||||||||
Sbjct:  1063  ttggggcgaggtgtacgcgagtgcgtgagtgcgtgagcgacagcagcatctttgtccagagccgga  1122

Query:  1111  actgcaactatcaacacggcttccaccagctaccgtctgcaagatcccagcggctgca  1170
              |||| ||  ||  ||||| ||| ||||||||||||| |||||||||||||||||||
```

FIG. 3C viii

```
Sbjct: 1123  actgcaactaccagcacggcttccaccggccactgtctgcaagatcccagtggctgca 1182
             |||||||||||||||||||||||||||||||||||||||||||||||||||||||||||

Query: 1171  gcctcaaggtcttcaacaaccagctcttcgctcagctcctggccag 1217
             |||||||||||||||||||||||||||||| |||| || |||||||
Sbjct: 1183  gcctcaaggtcttcaacaaccagctcttcgcccagctgctcgcccag 1229

Score = 285 bits (144),  Expect = 1e-73
Identities = 240/271 (88%), Gaps = 2/271 (0%)
Strand = Plus / Plus Query: 1198  tcgctcagctcctgcccagtcagttcaccacggctttgaagtcgtgtatgaactgacca 1257
             |||| ||||||||||||||||||||||||||||||||||||| || ||||||||||||||
Sbjct: 1222  tcgcccagctgctcgcccagtcagtgcaccacggctttgaagttgtctatgaactgacga 1281

Query: 1258  agatgtgtactatccggatgagttttgttaaggggtgctgagtatcatcgccagg 1317
             |||||||||| || || |||||||| |||| ||| |||||| || ||||||||||
Sbjct: 1282  agatgtgcacgattcggatgagctttgtgaagggctggggagccgagtatcatcgccagg 1341

Query: 1318  atgtcaccagcaccccctgctggattgagattcatcttcatgggccactgcagtggctgg 1377
```

FIG. 3C ix

```
Sbjct: 1342  atgtcacaagcaccccctgctggattgagattcatcttcatgaccactgcagtggttgg 1401

Query: 1378  acaaagttctgactcagatgggctctccacataaccccatttcttcagtgtcttaacagt 1437
             ||||  ||  || ||||||| |||||||||||  ||||| |||||||||||||||
Sbjct: 1402  acaaggtgctaactcagatgggctccccacacaacccctattcttcagtgtctta--agt 1459

Query: 1438  catgtcttaagctgcatttccataggataga 1468
             ||||| |||  |||||||||||| ||||||
Sbjct: 1460  catgtgctcagctgcatttccacagaataga 1490
```

FIG. 3C

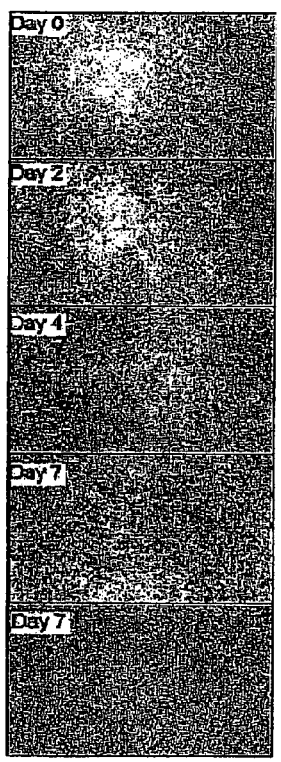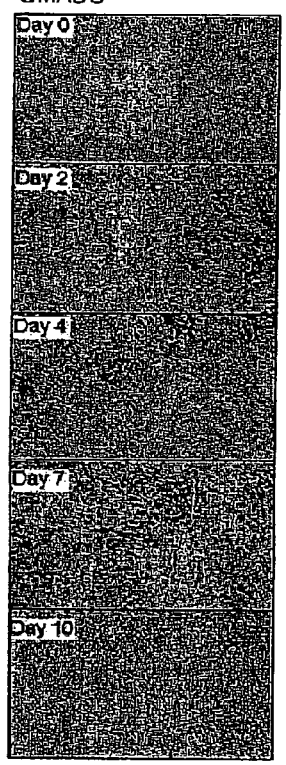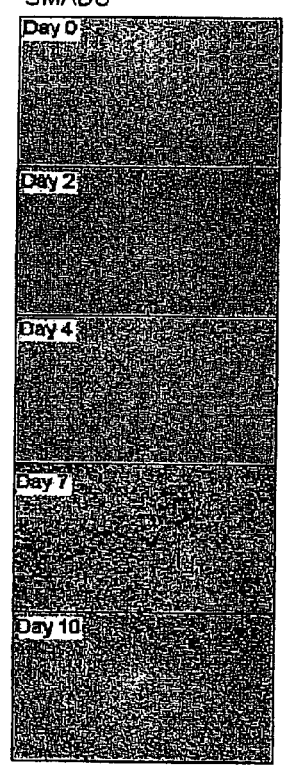
FIG.5A

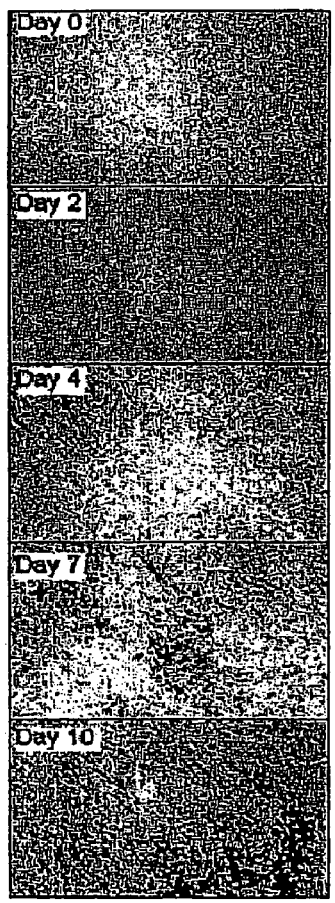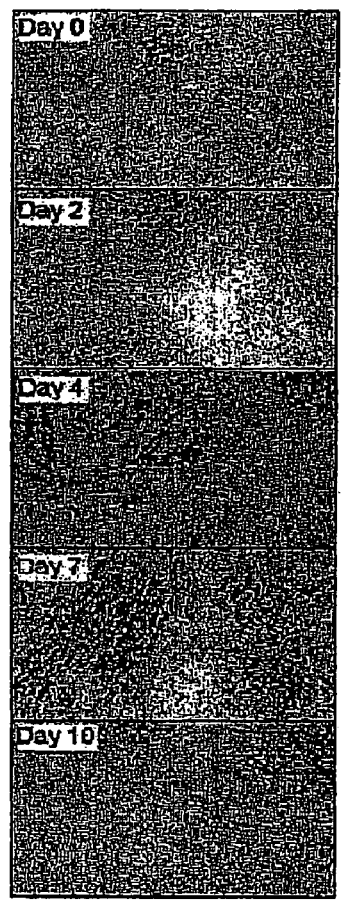
FIG.5B

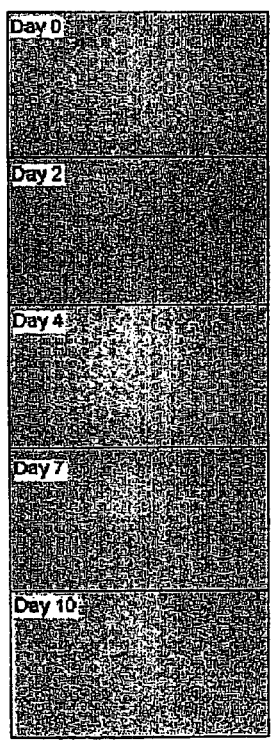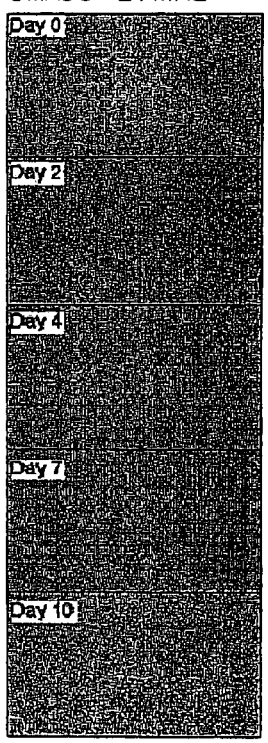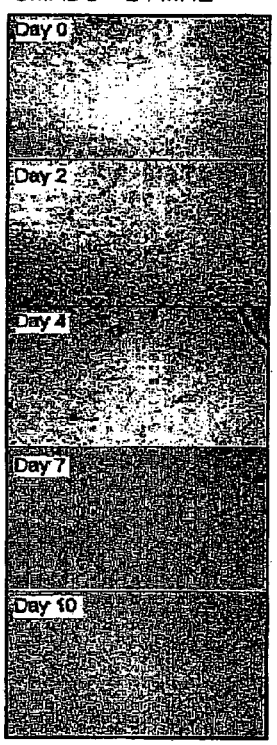
FIG.6

|  | C3H10T½ | C3H10T½ –BMP2 |
|---|---|---|
| Control | −2, 0, 2, 4, 7, 10, 13 [days post-confluence]<br>six1<br>osteocalcin<br>Collagen Ia 1<br>Collagen IIa 1<br>PTH/PTHrP<br>HPRT | −2, 0, 2, 4, 7, 10, 13 [days post-confluence]<br>six1<br>osteocalcin<br>Collagen Ia 1<br>Collagen IIa 1<br>PTH/PTHrPreceptor<br>HPRT |
| SMAD5 |  | six1<br>osteocalcin<br>Collagen Ia 1<br>Collagen IIa 1<br>PTH/PTHrP<br>HPRT |
| SMAD5 L+MH2 | six1<br>osteocalcin<br>Collagen Ia 1<br>Collagen IIa 1<br>PTH/PTHrP<br>HPRT | six1<br>osteocalcin<br>Collagen Ia 1<br>Collagen IIa 1<br>PTH/PTHrP<br>HPRT |
| SMAD8 |  | six1<br>osteocalcin<br>Collagen Ia 1<br>Collagen IIa 1<br>PTH/PTHrP<br>HPRT |
| SMAD8 L+MH2 | six1<br>osteocalcin<br>Collagen Ia 1<br>Collagen IIa 1<br>PTH/PTHrP<br>HPRT | six1<br>osteocalcin<br>Collagen Ia 1<br>Collagen IIa 1<br>PTH/PTHrP<br>HPRT |

FIG. 7

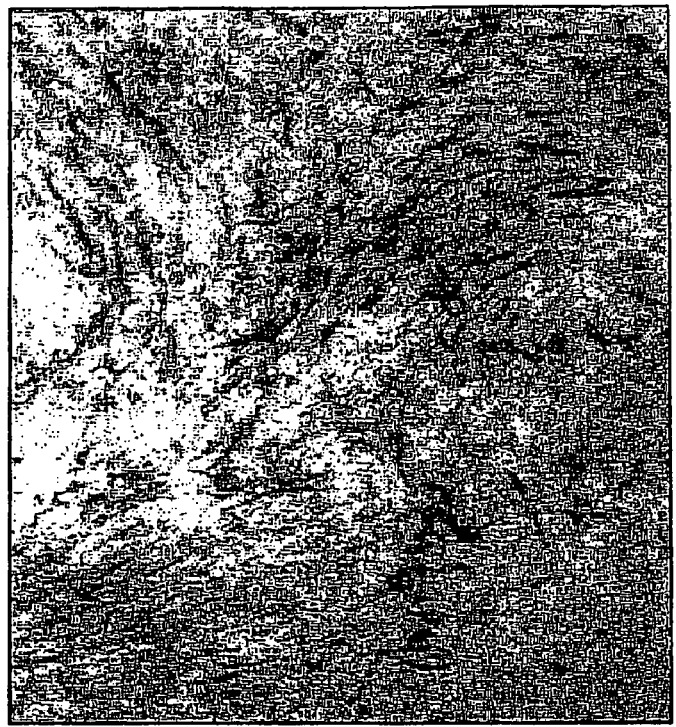
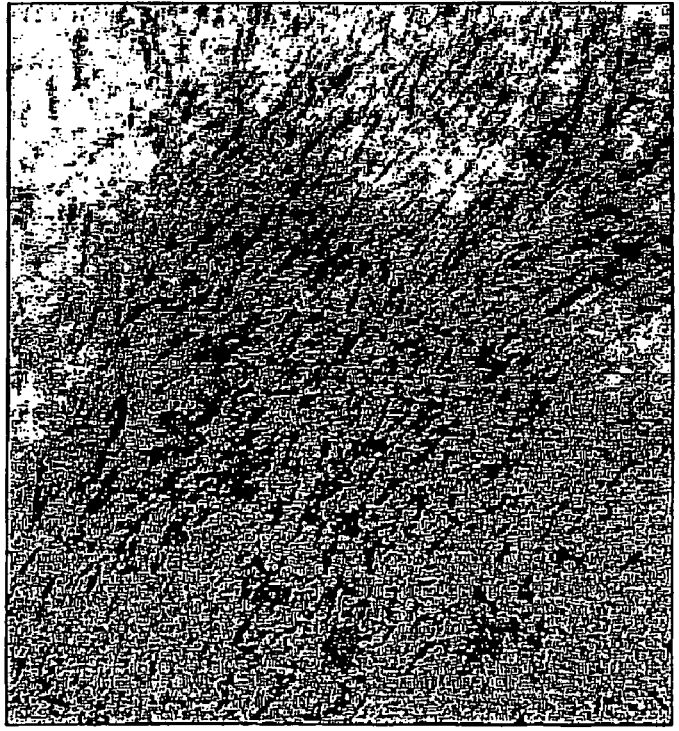
FIG. 8

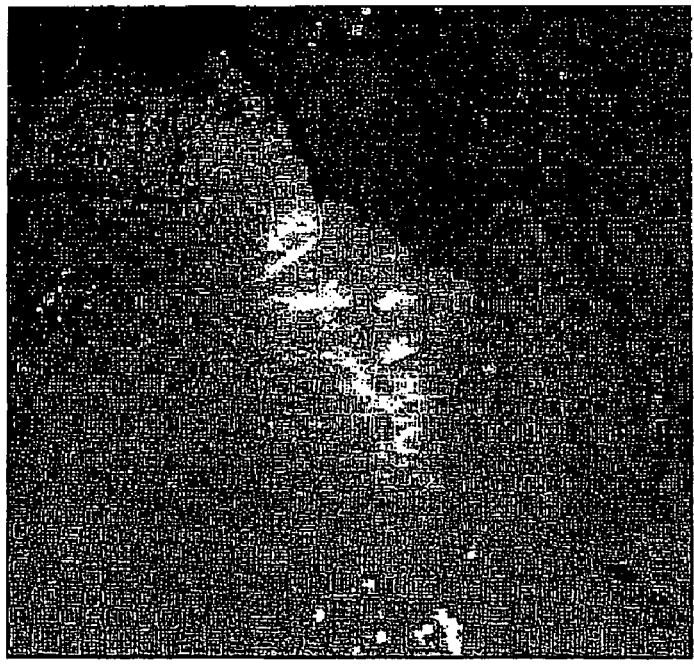
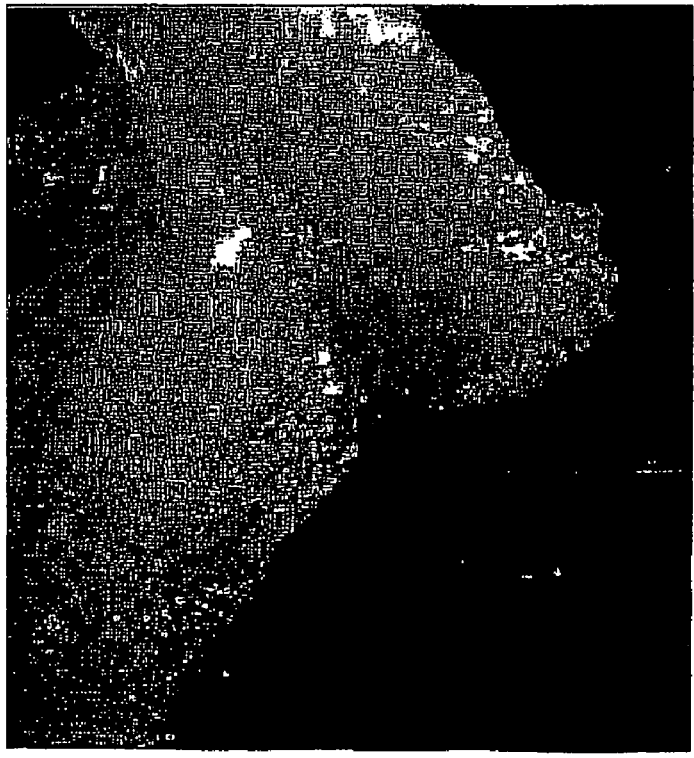
FIG.9A

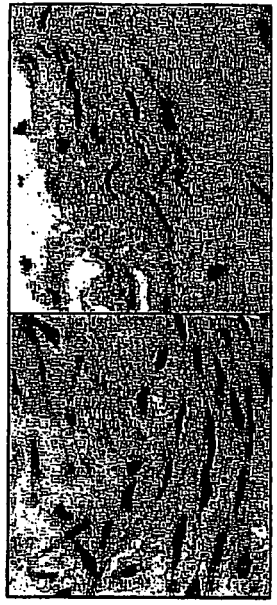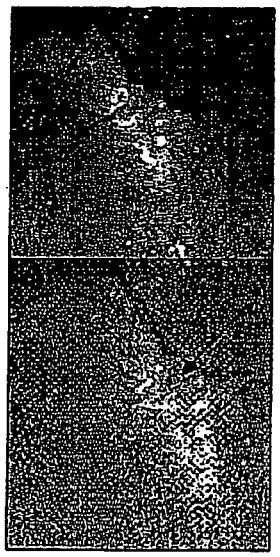
C3H10T1/2-BMP-2 SMAD 8 Cell Transplantation to C3H/HeN Mice, S.c. Injection Day 30
Microphotograph
x40
x100
FIG.9B

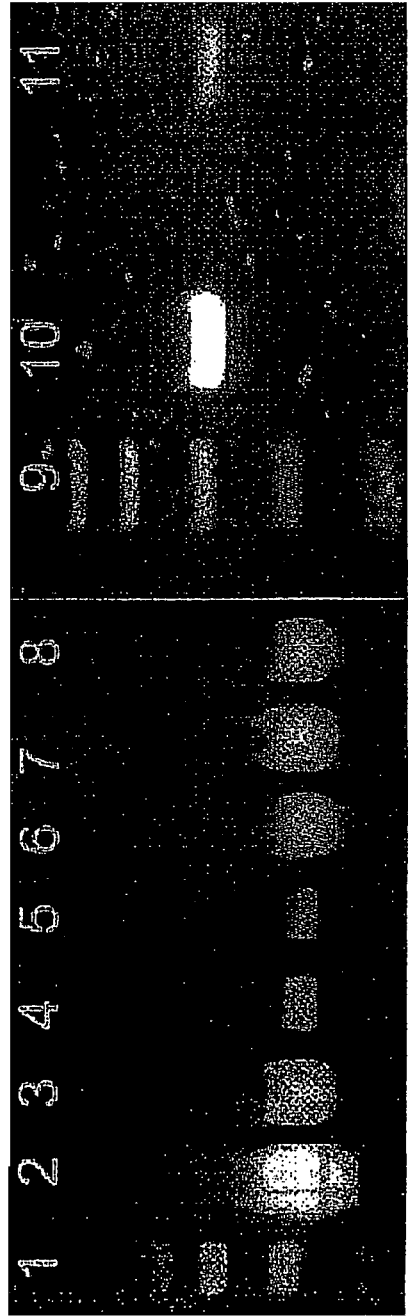

FIG.11

SMAD8 Gene is expressed in hAMSCs
Transfected with SMAD8 plasmid using the
Nucleofector™ system (Electroporation)

1– PCR Marker
2– SMAD8 plasmid (positive control)
3– Human AMSCs transfected with SMAD8 plasmid, after 10 days
4– Human AMSCs transfected with SMAD8 plasmid, after 15 days
5– Human AMSCs transfected with SMAD8 plasmid, after 15 days
6– Human AMSCs transfected with SMAD8&BMP2 plasmids, after 5 days
7– Human AMSCs transfected with SMAD8&BMP2 plasmids, after 5 days
8– Human AMSCs transfected with SMAD8&BMP2 plasmids, after 10 day
9– PCR Marker
10– SMAD8 plasmid (positive control)
11– Human AMSCs transfected with SMAD8 plasmid, after 5 days

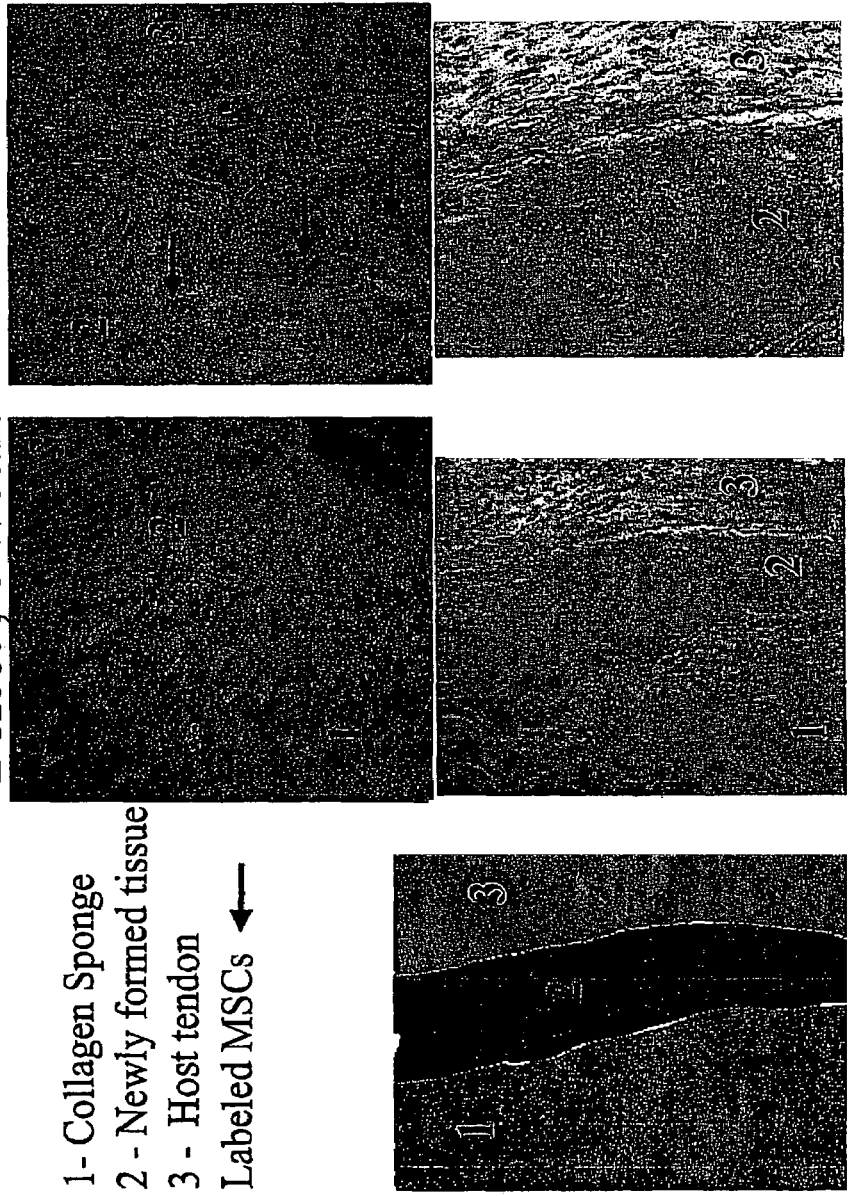
Fig. 13: Smad8/BMP2 MSCs in Rat Achilles Tendon Defect, 4 Weeks.
1 - Collagen Sponge
2 - Newly formed tissue
3 - Host tendon
Labeled MSCs ←

METHODS OF INDUCING OR ENHANCING CONNECTIVE TISSUE REPAIR

This application is a Continuation-in-Part application of U.S. Ser. No. 10/328,168, filed Dec. 26, 2002, which claims priority from provisional Application No. 60/342,375, filed Dec. 27, 2001, which are incorporated herein by reference.

FIELD OF THE INVENTION

This invention provides method for repairing, regenerating, treating, or inducing the repair of an injury, a defect or a condition of a connective tissue of a subject. This invention provides a method of regenerating, enhancing, inducing repair and/or development of connective tissue as a result of a defect, injury or condition of the connective tissue of a subject comprising the step of inserting an engineered cell which comprises a nucleic acid encoding a SMAD protein or variant thereof, so as to induce regeneration, repair and/or development of the connective tissue. This invention further provides methods of ex-vivo implantation of engineered cells into an injury, defect or condition of the connective tissue. This invention also provides a nucleic acid encoding a SMAD 8 protein variant, cells comprising such SMAD 8 variant, include mesenchymal stem cells, progenitor cells or cells derived from a connective tissue. Lastly, this invention provides SMAD 8 protein variant.

BACKGROUND OF THE INVENTION

Repair techniques for lacerated or severed tendons and ligaments ("connective tissues" or "cords") vary widely depending on the nature of the injury and the particular cord affected. There are large differences in the extent to which access can be obtained in the at least obtrusive manner, in the amount of cord excursion, in the surrounding environment, in the stresses to which different cords are normally subjected, and in the healing characteristics of different cords. In addition, often there is no consensus of the overall best way to repair a given cord. Examples of often injured cords having different accepted repair techniques are flexor tendons of the hand and the anterior cruciate ligament (ACL) of the knee.

For example, repair of a long flexor tendon that has been severed is typically achieved by suturing the severed tendon ends face-to-face. Historically, the joints across which the tendon acts were immobilized for from three to eight weeks to protect the tendon while it healed, because a freshly sutured tendon can withstand only a fraction of the tensile force to which a healthy tendon is subjected during normal use. Immobilization results in scarring and adhesion formation along the length of the tendon. Range of motion is adversely affected, particularly in the case of flexor tendons which normally glide smoothly through and over the unique system of tendon tunnels and pulleys of the hand. Nevertheless, it was thought that fibroblastic ingrowth was required in order for the tendon to heal, such that immobilization and the resulting decreased range of motion were considered necessary evils in order for effective healing to take place.

More recently, it has been discovered that flexor tendons have an intrinsic capacity to heal and that limited motion will actually expedite healing. The affected joints are most often partially immobilized to prevent inadvertent application of excess force.

In the case of an anterior cruciate ligament (connecting the bottom of the femur and the top of the tibia) the stresses resulting from applied forces are much greater, there is less interaction with surrounding tissue and bone, the excursion of the cord is less, and the healing tendencies are vastly different. Despite numerous studies, there still is no universally accepted repair procedure, and prevailing procedures are difficult and intricate. The current "standard of care" remains the reconstruction of the ACL using a bone-tendon-bone autograft (i.e., harvested from the patient). However, there are multiple problems with bone-tendon-bone grafting. (1) The intact ACL possesses important mechanoreceptive and proprioceptive capabilities. Graft reconstruction sacrifices these capabilities. (2) Autografting involves considerable donor site morbidity. (3) To avoid donor site morbidity, occasionally a cadaveric graft is used. This carries the risk of disease transmission.

Thus, it is highly advantageous to have an in vivo and ex vivo methods of inducing and/or enhancing the repair of damaged connective tissue.

SUMMARY OF THE INVENTION

This invention provides in one embodiment, a method of repairing or treating a connective tissue injury, defect or condition comprising the step of implanting an engineered cell which comprises a nucleic acid encoding a SMAD protein or variant thereof, so as to induce repair or treatment of the connective tissue. In one embodiment, the connective tissue is tendon. In another embodiment, the connective tissue is ligament. In another embodiment, the SMAD protein is a variant SMAD 8 protein. In another embodiment, the engineered cell comprises one or more nucleic acids which code for one or more proteins.

This invention provides in one embodiment, a method of regenerating connective tissue comprising the step of contacting said connective tissue and/or implanting the connective tissue with an engineered cell which comprises a nucleic acid encoding a SMAD protein or variant thereof, so as to regenerate said connective tissue. In one embodiment, the connective tissue is tendon. In another embodiment, the connective tissue is ligament. In another embodiment, the SMAD protein is a variant SMAD 8 protein. In another embodiment, the engineered cell comprises one or more nucleic acids which code for one or more proteins.

This invention provides in another embodiment, a method of inducing tendocyte differentiation comprising the step of contacting the tendocyte with: i) a cell comprising a vector having a nucleic acid encoding the SMAD protein or variant thereof; and/or ii) a vector having a nucleic acid encoding the SMAD protein or variant; and/or iii) a SMAD protein or variant; and/or iv) a nucleic acid encoding the SMAD protein or variant thereof, so as to induce tendocyte differentiation.

This invention provides in another embodiment a method of inducing ligament cell differentiation comprising the step of contacting the ligament cell with: i) a cell comprising a vector having a nucleic acid encoding the SMAD protein or variant thereof; and/or ii) a vector having a nucleic acid encoding the SMAD protein or variant; and/or iii) a SMAD protein or variant; and/or iv) a nucleic acid encoding the SMAD protein or variant thereof, so as to induce ligament cell differentiation.

This invention provides in another embodiment a method of augmenting direct repair of a connective tissue injury, defect and/or condition of a subject comprising the step of implanting an engineered cell which express a SMAD protein or variant thereof, so as to augment direct repair of the connective tissue.

This invention provides in another embodiment a method for ex-vivo connective tissue therapy comprising the steps of: i) obtaining one or more cells from a subject; ii) transfecting said cell(s) with a nucleic acid which encodes a SMAD protein, or variant thereof; and iii) implant said cell to the subject at the site of a connective tissue injury defect or condition. Such ex-vivo therapy may be used to repair, regenerate, and/or treat a connective tissue injury, defect and/or condition; and/or induce differentiation of ligament cells or tendocytes.

This invention provides in one embodiment, an engineered cell which comprises a nucleic acid which encodes a SMAD protein or variant thereof. In one embodiment is a progenitor cell. In another embodiment, the cell is a mesenchymal stem cell. In another embodiment, the cell comprises one or more additional isolated nucleic acids which encode for one or more proteins.

This invention further provides in one embodiment, an isolated amino acid sequence which encodes a variant SMAD 8 protein.

This invention further provides in another embodiment, an isolated nucleic acid sequence which encodes a variant SMAD 8 protein.

BRIEF DESCRIPTION OF THE DRAWINGS

FIGS. 1A and 1B: Nucleotide sequence of SMAD 8 protein (SEQ ID NO:3) and SMAD 8 L+MH2 domain (SEQ ID NO:4). The aminoterminal FLAG-Tag is indicated (shaded).

FIG. 2: Primary amino acid sequence of SMAD 8 protein (SEQ ID NO:5) and SMAD 8 L+MH2 domain (SEQ ID NO:6) used for expression studies. The aminoterminal FLAG-Tag is indicated (shaded).

FIGS. 3A-3C: Comparison of the primary amino acid sequence of SMADs. A. Comparison of rat and mouse SMAD 8 (SEQ ID NOs:8 and 7 respectively). The SMAD 8 variant consists of the linker region beginning with "SEYNPQLSLLAF . . . to . . . NPISSVS" within the SMAD 8 protein; B. Comparison of mouse SMAD 5 (SEQ ID NO:9) and SMAD 8 (SEQ ID NO:8) MH1, Linker, and MH2 domains are indicated. C. Comparison of human SMAD 8 (SEQ ID NO: 10) to mouse SMAD 8 (SEQ ID NO:12).

FIGS. 5A-5B: Cellular phenotypes in C3H10T1/2-BMP2 by forced expression of SMAD-variants.

FIG. 6: Cellular phenotypes in C3H10T1/2$^{WT}$ by forced expression of SMAD-variants.

FIG. 7: RT-PCR analyses of expression levels of chondrogenic, ostesteogenic and tendogenic markers.

FIG. 8: Tendogenic phenotype in C3H10T1/2-BMP2 by forced expression of SMAD 8 protein L+MH2.

FIGS. 9A-9C: Ectopic ligament formation of C3H10T1/2-BMP2/SMAD-8 protein L+MH2 after intramuscular transplantation.

FIG. 11: Demonstrates expression of SMAD 8 gene in hAMSCs transfected with SMAD 8 plasmid using by electroporation.

FIG. 13. Demonstrates the engraftment of engineered cell, specifically a mesenchymal stem cell expressing a SMAD 8 variant gene in an Achilles tendon defect of 3×3 mm (shown in FIG. 12).

DETAILED DESCRIPTION OF THE EMBODIMENTS

Figure 1B:
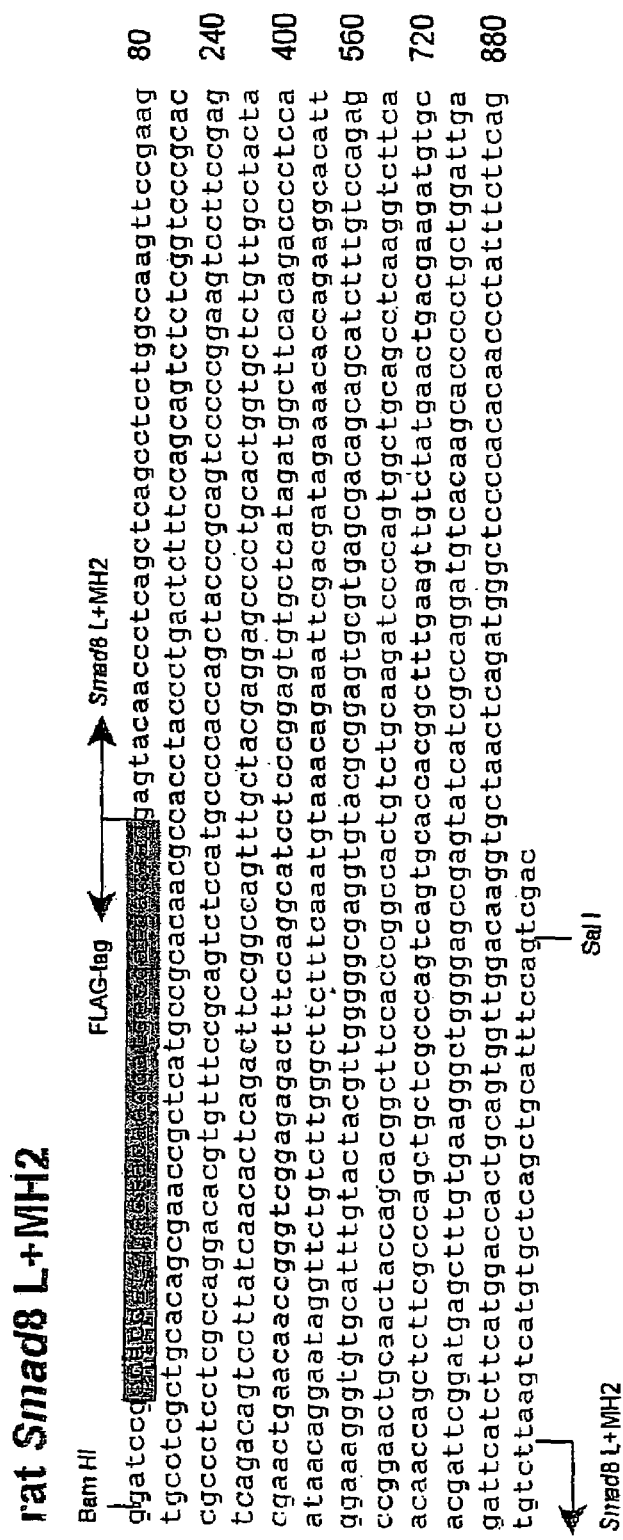

This invention provides methods for regenerating, repairing, and/or treating connective tissue injuries, defects, injuries and/or conditions. In one embodiment, this invention provides a method of repairing or treating a connective tissue injury, defect or condition comprising the step of implanting an engineered cell which comprises a nucleic acid encoding a SMAD protein or variant thereof, so as to induce repair or treatment of the connective tissue. In one embodiment, the connective tissue is tendon. In another embodiment, the connective tissue is ligament. In another embodiment, the cell is an adult mesenchymal stem cell from the bone marrow. In another embodiment, the SMAD protein is a SMAD 8 protein. In another embodiment, the SMAD 8 protein is a variant SMAD 8 protein. In another embodiment, the cell comprises one or more nucleic acids which code for one or more proteins.

This invention provides in one embodiment, a method of regenerating connective tissue comprising the step of contacting said connective tissue and/or implanting the connective tissue with an engineered cell which comprises a nucleic acid encoding a SMAD protein or variant thereof, so as to regenerate said connective tissue. In one embodiment, the connective tissue is tendon. In another embodiment, the connective tissue is ligament. In another embodiment, the cell is an adult mesenchymal stem cell from the bone marrow. In another embodiment, the SMAD protein is a SMAD 8 protein. In another embodiment, the SMAD 8 protein is a variant SMAD 8 protein. In another embodiment, the cell comprises one or more nucleic acids which code for one or more proteins.

This invention provides in another embodiment, a method of inducing tendocyte differentiation comprising the step of contacting the tendocyte with: i) a cell comprising a vector having a nucleic acid encoding the SMAD protein or variant thereof; and/or ii) a vector having a nucleic acid encoding the SMAD protein or variant; and/or iii) a SMAD protein or variant; and/or iv) a nucleic acid encoding the SMAD protein or variant thereof, so as to induce tendocyte differentiation. In another embodiment, the cell is an adult mesenchymal stem cell from the bone marrow. In another embodiment, the SMAD protein is a SMAD 8 protein. In another embodiment, the SMAD 8 protein is a variant SMAD 8 protein. In another embodiment, the cell comprises one or more nucleic acids which code for one or more proteins.

This invention provides in another embodiment a method of inducing ligament cell differentiation comprising the step of contacting the ligament cell with: i) a cell comprising a vector having a nucleic acid encoding the SMAD protein or valiant thereof; and/or ii) a vector having a nucleic acid encoding the SMAD protein or variant; and/or iii) a SMAD protein or variant; and/or iv) a nucleic acid encoding the SMAD protein or variant thereof, so as to induce ligament cell differentiation. In another embodiment, the cell is an adult mesenchymal stem cell from the bone marrow. In another embodiment, the SMAD protein is a SMAD 8 protein. In another embodiment, the SMAD 8 protein is a variant SMAD 8 protein. In another embodiment, the cell comprises one or more nucleic acids which code for one or more proteins.

This invention provides in another embodiment a method of augmenting direct repair of a connective tissue injury, defect and/or condition of a subject comprising the step of implanting an engineered cell which express a SMAD protein or variant thereof, so as to augment direct repair of the connective tissue. In one embodiment, the connective tissue is tendon. In another embodiment, the connective tissue is ligament. In another embodiment, the cell is an adult mesenchymal stem cell from the bone marrow. In another embodiment, the SMAD protein is a SMAD 8 protein. In another embodiment, the SMAD 8 protein is a variant SMAD 8 protein. In another embodiment, the cell comprises one or more nucleic acids which code for one or more proteins.

As used herein, the term "connective tissue" includes but is not limited to in one embodiment ligament tissue. In another embodiment a tendon tissue. In another embodiment a cartilage tissue. In another embodiment skin. In another embodiment bone. In another embodiment intervertebral disc. In another embodiment dental pulp. In another embodiment dentin. In another embodiment gingival. In another embodiment periodontal ligament.

The term "ligament" is referred hereinabove to both the rope-like structures of white fibrous connective tissue, which attach anterior extremities of interacting bones, as well as the tissue defining a synovial capsule. In one embodiment, the ligament is anterior cruciate ligament. In another embodiment, the ligament is a posterior cruciate ligament. In another embodiment, the ligament is a tibial collateral ligament. In another embodiment, the ligament is a fibular collateral ligament. In another embodiment, the ligament is a transverse ligament. In another embodiment, the ligament is a posterior menisco-femoral ligament. In another embodiment, the ligament is a posterior superior tibiofibular ligament. In another embodiment, the ligament is a lateral collateral ligament, which is a complex of three ligaments that helps support the lateral side of the ankle joint. Individually, these ligaments are known as the anterior talofibular, lcaneofibular and the posterior talofibular ligaments.

The term "tendon" is intended to define the connective tissue structure, which joins muscle to bone for example, without being limited, in one embodiment the tendon may be the achilles tendon, which is a tendon formed by the union of two muscles, the gastrocnemius and the soleus, which join in the mid-calf area and are known as the gastroc-soleal complex or Latissimus Dorsi Tendon, posterior tibial tendon, patellar tendon, plantar flexor muscle-tendon unit. In another embodiment the tendon is rotator cuff tendon.

In one embodiment, the cell is an engineered cell which comprises a nucleic acid which encodes a SMAD protein, and/or SMAD 8 protein, and/or a variant SMAD 8 protein. In another embodiment, the cell comprises one or more additional isolated nucleic acids which encode for one or more proteins. As defined herein the cell is in one embodiment a progenitor cell. In another embodiment, the cell is a mesenchymal stem cell. In another embodiment the mesenchymal Stem cell is an adult mesenchymal Stem cell from the bone marrow. In another embodiment, the cell is derived from the ligament or from the tendon. In another embodiment, the cell types which can be used are fibroblasts from connective tissue in skin and gingiva.

In another embodiment, the engineered cell is transfected to comprise one or more additional nucleic acids which express a protein which activates the BMP mediated signaling pathway. Thus, the cell is engineered to express, for example without limitation, SMAD, and/or SMAD 8 or variant, analog, fragment, mimetic, mutant or synthetic thereof, and additionally a BMP and/or variant, analog, fragment, mimetic, mutant or synthetic thereof. In one embodiment, the engineered cell is transfected with a nucleic acid which encodes a variant SMAD 8 and additionally a nucleic acid which encodes BMP 2. This invention provides in one embodiment, an engineered mesenchymal stem cell which comprises a nucleic acid which encodes a SMAD 8 variant protein In another embodiment, the cell comprises one or more additional isolated nucleic acids which encode for one or more proteins.

In another embodiment, there is provided a composition comprising the engineered cell. In another embodiment there is provided a pharmaceutical composition which comprises the engineered cell and an acceptable diluent or carrier. For example, the composition comprises an engineered mesenchymal stem cell which comprises a nucleic acid which encodes a SMAD 8 variant protein. In another embodiment, the cell comprises one or more additional isolated nucleic acids which encode for one or more proteins.

In another embodiment, there is provided an implant device comprising the engineered cell which expresses a SMAD protein, SMAD 8 protein, or variant thereof, analog, fragment, mimetic, mutant or synthetic thereof. In another embodiment the device further expressing at least one protein which activates BMP mediated signaling pathway.

This invention provides in another embodiment a method for ex-vivo connective tissue therapy comprising the steps of: i) obtaining one or more cells from a subject; ii) transfecting said cell(s) with a nucleic acid which encodes a SMAD protein, or variant thereof; and iii) implant said cell to the subject at the site of a connective tissue injury defect or condition. Such ex-vivo therapy may be used to repair, regenerate, and/or treat a connective tissue injury, defect and/or condition; and/or induce differentiation of ligament cells or tendocytes. Such cells are implanted or transplanted into the subject. The implant or transplant may be in a carrier.

Methods of obtaining adult mesenchymal stem cells from the bone marrow for autologous therapy are known to those skilled in the art. Further, methods of culturing, propagating, growing and/or differentiating such cells and producing an engineered cell are known to those skilled in the art. Further, methods of implanting the engineered cell into the site of the connective tissue injury or defect or condition are known to those skilled in the art. For example, an amount of engineered cells may be implanted into the subject in a carrier as defined hereafter. As contemplated by this invention, the implant or transplant may be in the site of the injury, defect or condition or may be adjacent to such injury, defect or condition. In one embodiment, the adult mesenchymal stem cell is a mammalian mesenchymal stem cell. In another embodiment, the adult mesenchymal stem cell is a human mesenchymal stem cell. In another embodiment, the adult mesenchymal stem cell is a mouse mesenchymal stem cell. In another embodiment, the adult mesenchymal stem cell is a rat mesenchymal stem cell.

The effective amount of engineered adult mesenchymal stem cells is the amount of the cells which express an effective amount of the SMAD 8 variant protein to differentiate the mesenchymal stem cell to a tendon tissue in the subject. Such an amount depends on the amount of tendon or ligament tissue desired to be formed, the site of tendon or ligament damage, the condition of the damaged tendon or ligament, the size of a wound, type of damaged tissue, the patient's age, sex, and diet, the severity of any infection, time of administration and other clinical factors. The dosage may vary with the type of carrier used. The addition of other known proteins and/or factors to the final composition, may also affect the dosage. In one embodiment the amount of cells implanted in the injury, defect or condition is in a range of 150,000 to 12,000,000. In another embodiment the range is 500,000 to 8,000,000. In another embodiment the range is 750,000 to 5,000,000. In another embodiment the range is 1,000,000 to 5,000,000. In one embodiment the amount of cells implanted in the injury, defect or condition is 500,000. In one embodiment the amount of cells implanted in the injury, defect or condition is 750,000. In one embodiment the amount of cells implanted in the injury, defect or condition is 1,000,000. In one embodiment the amount of cells implanted in the injury, defect or condition is 1,250,000. In one embodiment the amount of cells implanted in the injury, defect or condition is 1,500,000. In one embodiment the amount of cells implanted in the injury, defect or condition is 1,750,000. In one embodiment the amount of cells implanted in the injury, defect or condition is 2,000,000. In one embodiment the amount of cells implanted in the injury, defect or condition is 2,250,000. In one embodiment the amount of cells implanted in the injury, defect or condition is 2,500,000. In one embodiment the amount of cells implanted in the injury, defect or condition is 2,750,000. In one embodiment the amount of cells implanted in the injury, defect or condition is 3,000,000. In one embodiment the amount of cells implanted in the injury, defect or condition is 4,000,000.

The differentiation, repair, regeneration, or treatment can be monitored by periodic assessment of tendon/ligament-like tissue formation, or tendon or ligament growth and/or repair. The progress can be monitored by methods known in the art, for example, X-rays (CT), ultra-sound, MRI, arthroscopy and histomorphometric determinations.

The term "SMAD protein" includes but is not limited to SMAD-1, SMAD-2, SMAD-3, SMAD-4, SMAD-5, SMAD-6, SMAD-7 or SMAD-8. SMAD is defined as a family of intracellular signaling proteins in vertebrates, which transduce signals for members of the TGF-β superfamily. In another embodiment, "SMAD protein" includes, but is not limited to, a variant, an analog a, fragment, synthetic, mutant or a mimetic.

As contemplated herein, the nucleic acid which encodes SMAD protein includes mammalian SMAD nucleic acids and is not limited to the nucleic acid deposited in Genebank having Accession No. NM 005905, NT 016606, NM 008539, AF 067727, NM 010754, AB 071949, AH006488, AF 056001, AB 008192, NM 005902, NM 016769, NT 010265, NT 033905, AB 043547, AB 010954, AF 056002, NT 016714, AH005750, AH-005612, MN 008541, AB043547, AH008461, AF037469, AF 043640, AH011391, AH008243, AJ000550, AF175408, and MN 139972, MN 005905, MN 19483, and/or SEQ ID NO. 1 and/or 2, and/or the nucleic acid sequence as shown in FIGS. 1-3.

As contemplated by this invention, this invention provides a nucleic acid which encodes a SMAD protein when the nucleic acid is 72%, or 74%, or 76%, or 78%, or 82%, or 84%, or 85%, or 87%, or 90%, or 92%, or 95%, or 98% identical to the nucleic acid sequence as shown NM 005905, NT 016606, NM 008539, AF 067727, NM 010754, AB 071949, AH006488, AF 056001, AB 008192, NM 005902, NM 016769, NT 010265, NT 033905, AB 043547, AB 010954, AF 056002, NT 016714, AH005750, AH 005612, MN 008541, AB043547, AH008461, AF037469, AF 043640, AH011391, AH008243, AJ000550, AF175408, and MN 139972 MN 005905, MN 19483, and/or SEQ ID NO. 1 and/or 2, and/or the nucleic acid sequence as shown in FIGS. 1-3.

Figure 3A:
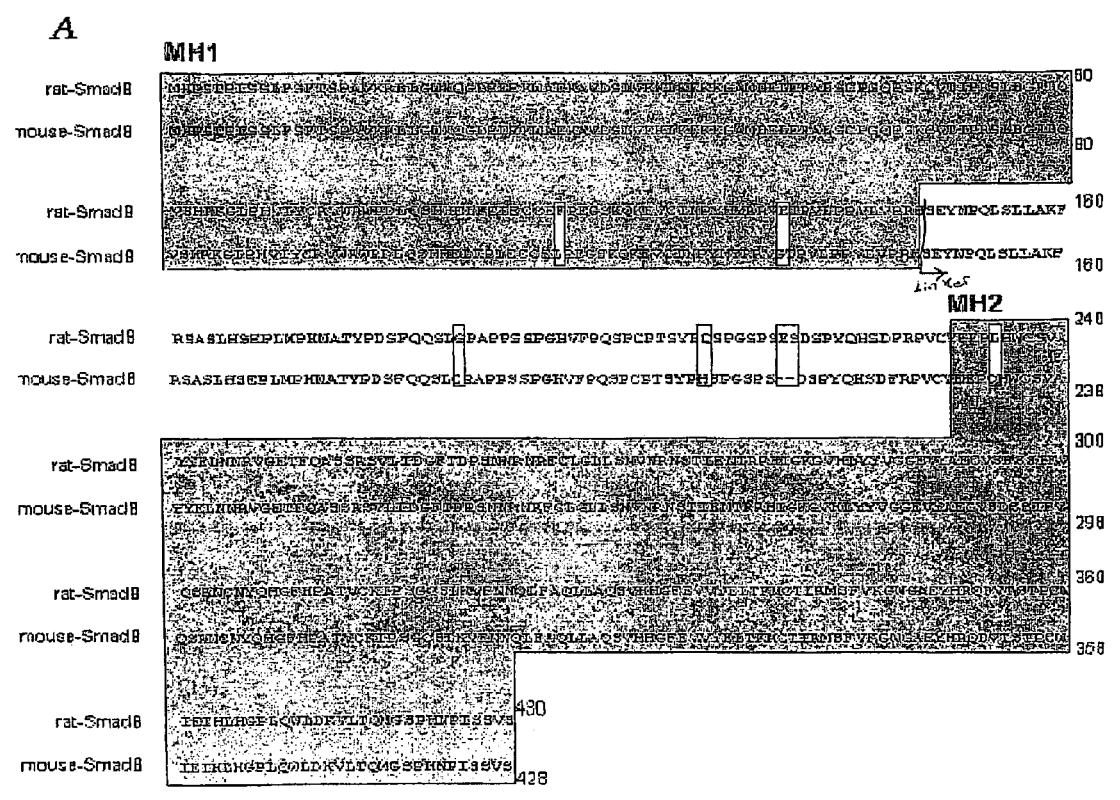

In one embodiment, a vector comprises the nucleic acid sequence within the MH1, Linker region and a MH2 region as shown in FIG. 3A. In one embodiment, a vector comprises the nucleic acid sequence within the Linker region and a MH2 region as shown in FIG. 3A In another embodiment the vector comprises the nucleic acid sequence within a MH2 region as shown in FIG. 3A. In one embodiment, a vector comprises the nucleic acid sequence which codes for the amino acid sequence as shown within the MH1, Linker region and a MH2 region as shown in FIG. 3A. In one embodiment, a vector comprises the nucleic acid sequence which codes for the amino acid sequence as shown within the Linker region and a MH2 region as shown in FIG. 3A In another embodiment the vector comprises the nucleic acid sequence which codes for the amino acid sequence as shown within a MH12 region as shown in FIG. 3A. In one embodiment, the vector comprises the nucleic acid which codes for the amino acid as set forth in SEQ ID. No. 1. In one embodiment, the vector comprises the nucleic acid which codes for the amino acid as set forth in SEQ ID. No. 2. Further, in another embodiment, as contemplated by this invention, the amino acid sequence of the variant SMAD 8 protein is 72%, or 74%, or 76%, or 78%, or 80%, or 82%, or 84%, or 85%, or 88%, or 90%, or 92%, or 95%, or 98% identical to the amino acid sequence as set forth in SEQ ID Nos 1 or 2.

In one embodiment, the engineered cell or adult mesenchymal stem cell expresses the variant SMAD 8 protein comprising the nucleic acid sequence within the Linker region and a MH2 region as shown in FIG. 3A. In another embodiment the engineered cell or adult mesenchymal stem cell expresses the variant SMAD 8 protein which encodes a variant SMAD 8 comprising the nucleic acid sequence within the a MH2 region as shown in FIG. 3A. In one embodiment, the engineered cell or adult mesenchymal stem cell expresses the variant SMAD 8 protein as set forth in SEQ ID. No. 1. In one embodiment, the engineered cell or adult mesenchymal stem cell expresses the variant SMAD 8 protein as set forth in SEQ ID. No. 2. Further, in another embodiment, as contemplated by this invention, the amino acid sequence of the variant SMAD 8 protein is 72%, or 74%, or 76%, or 78%, or 80%, or 82%, or 84%, or 85%, or 88%, or 90%, or 92%, or 95%, or 98% identical to the amino acid sequence as set forth in SEQ ID Nos 1 or 2.

This invention further provides an isolated nucleic acid sequence which encodes a mammalian variant SMAD 8 protein. This invention further provides an isolated amino acid sequence which encodes a mammalian variant SMAD 8 protein. The mammalian variant may be rat, mouse, rabbit, goat, horse, pig, or human. In another embodiment, the variant SMAD 8 is human.

As defined herein, a SMAD 8 variant means in one embodiment a nucleic acid which encodes a variant SMAD 8 protein comprising the nucleic acid sequence within the Linker region and a MH2 region as shown in FIG. 3A. In another embodiment the variant SMAD 8 is a nucleic acid which encodes a variant SMAD 8 comprising the nucleic acid sequence within the a MH2 region as shown in FIG. 3A. In another embodiment, the variant SMAD 8 is a nucleic acid which encodes a variant SMAD 8 comprising the nucleic acid which codes for an amino acid sequence as set forth in SEQ ID NO 1. In another embodiment, the variant SMAD 8 is a nucleic acid which encodes a variant SMAD 8 comprising the nucleic acid which codes for an amino acid sequence as set forth in SEQ ID NO 2. In another embodiment, the variant SMAD 8 comprises the amino acid sequence as set forth in SEQ ID No. 1. In another embodiment, the variant SMAD 8 comprises the amino acid sequence as set forth in SEQ ID No. 2.

As provided herein, in one embodiment the amino acid sequence of the variant human SMAD 8 is:

(SEQ ID NO 1)

EEPQHWCSVAYYELNNRVGETFQASSRSVLIDGFTDPSNNRNRFCL
GLLSNVNRNSTEIENTRRHIGKGVHLYYVGGEVYAECVSDSSIFVQS
RNCNYQHGFHPATVCKIPSGCSLKVFNNQLFAQLLAQSVHHGFEV
VYELTKMCTIRMSFVKGWGAEYHRQDVTSTPCWIEIHLHGPLQWL
DKVKTQMGSPHNPISSVS.

As provided herein, in one embodiment the amino acid sequence of the variant human SMAD 8 is:

(SEQ ID NO. 2)

EEPQHWCSVAYYELNNRVGETFQASSRSVLIDGFTDPSNNRNRFCL
GLLSNVNRNSTEIENTRRHIGKGVHLYYVGGEVYAECVSDSSIFVQS
RNCNYQHGFHPATVCKIPSGCSLKVFNNQLFAQLLAQSVHHGFEV
VYELTKMCTIRMSFVKGWGAEYHRQDVTSTPCWIEIHLHGPLQWL
DKVKTQMGSPHNPISSVS

In one embodiment, as contemplated by this invention, this invention provides a nucleic acid which encodes a variant SMAD 8 protein wherein the nucleic acid shown in FIG. 3C.

In another embodiment, the SMAD-8 variant is a rat SMAD-8 variant. In another embodiment it is a mouse Variant SMAD-8 protein and in another embodiment it is a human SMAD-8 variant.

As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotide. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

The terms "protein", "polypeptide" and "peptide" are used interchangeably herein when referring to a gene product.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared with the wild type sequence, while the sequence still encodes a protein or peptide, or fragments thereof, that retain their wild type function despite these variations. Proteins, protein fragments, peptides, or derivatives also can experience deviations from the wild type from which still functioning in the same manner as the wild type form. Similarly, derivatives of the genes and products of interest used in the present invention will have the same biological effect on the host as the non-derivatized forms. Examples of such derivatives include but are not limited to dimerized or oligomerized forms of the genes or proteins, as wells as the genes or proteins. Biologically active derivatives and fragments of the genes, DNA sequences, peptides and proteins of the present invention are therefore also within the scope of this invention. In addition, any nucleic acid which is cis acting and integrated upstream to an endogenous SMAD nucleic acid sequence or to a nucleic acid encoding for a protein which activates the BMP mediated signaling pathway and therefore induce increase in the level of SMAD or in the a protein which activates the BMP mediated signaling pathway, respectively, is relevant to the present invention. The invention provides in another embodiment, a composition comprising a recombinant vector which comprises at least one nucleic acid sequence encoding the SMAD protein or variant, analog, fragment, mimetic, mutant or synthetic thereof, at least one nucleic acid sequence which encodes for at least one protein which activates the BMP mediated signaling pathway and a pharmaceutically active carrier.

In another embodiment, the nucleic acid sequences described in the present invention can be either present in a cis form, i.e. on the same recombinant vector, or alternatively, are expressed by two different vectors (trans form). For example, the composition of the present invention may include a vector comprising a nucleic acid which encodes for SMAD-8 and/or another nucleic acid which encodes for BMP2 protein, or in another embodiment the composition may include two different vectors; one which include a nucleic acid sequence which encodes for SMAD-8 and another vector which include a nucleic acid which encodes for BMP2 protein. The expression can be at the same time, or can be controlled by different regulatory units.

The term "cis-acting" is used to describe a genetic region that serves as an attachment site for DNA-binding proteins (e.g. enhancers, operators and promoters) thereby affecting the activity of genes on the same chromosome.

As a new and specific nucleotide sequence is disclosed herein, the artisan will recognize that the nucleic acid can be produced by any synthetic or recombinant process such as is well known in the art. Nucleic acids according to the invention can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

Methods for modifying nucleic acids to achieve specific purposes are disclosed in the art, for example, in Sambrook et al. (1989). Moreover, the nucleic acid can include one or more portions of nucleotide sequence that are non-coding for the protein of interest. The invention further provides, DNA sequences which encode proteins similar to the protein encoded by the SEQ ID. No. 1, but which differ in codon sequence due to the degeneracies of the genetic code or allelic variations (naturally-occurring base changes in the species population which may or may not result in an amino acid change) also encode the proteins of the invention described herein. Variations in the DNA sequences which are caused by point mutations or by induced modifications (including insertion, deletion, and substitution) to enhance the activity, half-life or production of the polypeptides encoded thereby are also encompassed in the invention.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together. See, generally, Sambrook et al. (1989) and Glover et al. (1995). DNA expressing functional homologs of the protein can be prepared from wild-type DNA by site-directed mutagenesis. See, for example, Zoller et al. (1982);

Zoller (1983); and Zoller (1984); McPherson (1991). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989). It is convenient to amplify the clones in the lambda-gt10 or lambda-gt11 vectors using lambda-gt10- or lambda-gt11-specific oligomers as the amplimers (available from Clontech, Palo Alto, Calif.).

Larger synthetic nucleic acid structures can also be manufactured having specific and recognizable utilities according to the invention. For example, vectors (e.g., recombinant expression vectors) are known which permit the incorporation of nucleic acids of interest for cloning and transformation of other cells. Thus, the invention further includes vectors (e.g., plasmids, phages, cosmids, etc.) which incorporate the nucleotide sequence of the invention, especially vectors which include the gene for expression of the protein encoded by the nucleic acid of the invention.

The DNA of the invention can be replicated and used to express recombinant protein following insertion into a wide variety of host cells in a wide variety of cloning and expression vectors. The host can be prokaryotic or eukaryotic. The DNA can be obtained from natural sources and, optionally, modified. The genes can also be synthesized in whole or in part.

In order to generate the nucleic acid constructs of the present invention disclosed hereinbelow, polynucleotide segments can be ligated into commercially available expression construct systems suitable for transforming bacterial cells and for directing the expression of the fusion protein within the transformed cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides, and as such, encompass preferred embodiments of the present invention.

Suitable bacterial expression constructs for use with the present invention include, but are not limited to the pCAL, pUC, pET, pETBlue™ (Novagen), pBAD, pLEX, pTrcHis2, pSE280, pSE380, pSE420 (Invitrogen), pKK223-2 (Clontech), pTrc99A, pKK223-3, pRIT2T, pMC1871, pEZZ 18 (Pharmacia), pBluescript II SK (Stratagene), pALTER-Ex1, pALTER-Ex2, pGEMEX (Promega), pFivE (MBI), pQE (Qiagen) commercially available expression constructs, and their derivatives. In preferred embodiments of the present invention the construct may also include, a virus, a plasmid, a bacmid, a phagemid, a cosmid, or a bacteriophage.

Nucleotide sequences are typically operably linked to, i.e., positioned, to ensure the functioning of an expression control sequence. These expression constructs are typically replicable in the cells either as episomes or as an integral part of the cell's chromosomal DNA, and may contain appropriate origins of replication for the respective prokaryotic strain employed for expression. Commonly, expression constructs contain selection markers, such as for, example, tetracycline resistance, ampicillin resistance, kanamycin resistance or chlormaphenicol resistance, facilitating detection and/or selection of those bacterial cells transformed with the desired nucleic acid sequences (see, e.g., U.S. Pat. No. 4,704,362). These markers, however, are not exclusionary, and numerous others may be employed, as known to those skilled in the art. Indeed, in a preferred embodiment of the present invention expression constructs contain both positive and negative selection markers.

Similarly reporter genes may be incorporated within expression constructs to facilitate identification of transcribed products. Accordingly, in a preferred embodiment of the present invention, reporter genes utilized are selected from the group consisting of β-galactosidase, chloramphenicol acetyl transferase, luciferase and a fluorescent protein.

Prokaryotic promoter sequences regulate expression of the encoded polynucleotide sequences, and in preferred embodiments of the present invention, are operably linked to polynucleotides encoding the SMAD derived peptide, signal sequence and polynucleotides encoding the protein-of-interest. In additional preferred embodiments of the present invention, these promoters are either constitutive or inducible, and provide a means of high and low levels of expression of the fusion polypeptides.

Many well-known bacterial promoters, including the T7 promoter system, the lactose promoter system, typtophan (Trp) promoter system, Trc/Tac Promoter Systems, beta-lactamase promoter system, tetA Promoter systems, arabinose regulated promoter system, Phage T5 Promoter, or a promoter system from phage lambda, may be employed, and others, as well, and comprise preferred embodiments of the present invention. The promoters will typically control expression, optionally with an operator sequence and may include ribosome binding site sequences for example, for initiating and completing transcription and translation. According to additional preferred embodiments, the vector may also contain expression control sequences, enhancers that may regulate the transcriptional activity of the promoter, appropriate restriction sites to facilitate cloning of inserts adjacent to the promoter and other necessary information processing sites, such as RNA splice sites, polyadenylation sites and transcription termination sequences as well as any other sequence which may facilitate the expression of the inserted nucleic acid.

Incorporation of recombinant nucleic acid within cells can be accomplished through a number of methods well known in the art. Nucleic acid constructs can be utilized to stably or transiently transduce the micro-organ cells. In stable transduction, the nucleic acid molecule is integrated into the cells genome and as such it represents a stable and inherited trait. In transient transduction, the nucleic acid molecule is maintained in the transduced cells as an episome and is expressed by the cells but it is not integrated into the genome. Such an episome can lead to transient expression when the transduced cells are rapidly dividing cells due to loss of the episome or to long term expression wherein the transduced cells are non-dividing cells.

Typically the nucleic acid sequence is subcloned within a particular vector, depending upon the preferred method of introduction of the sequence within cells. Once the desired nucleic acid segment is subcloned into a particular vector it thereby becomes a recombinant vector. To generate the nucleic acid constructs in context of the present invention, the polynucleotide segments encoding sequences of interest can be ligated into commercially available expression vector systems suitable for transducing mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

There are a number of techniques known in the art for introducing the above described recombinant vectors into cells of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation, liposome-mediated transfection, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged.

In another preferred embodiment of the present invention, exogenous polynucleotide introduction into micro-organs is via ex-vivo transduction of the cells with a viral or non-viral vector encoding the sequence of interest.

In another embodiment, the vector further comprises a nucleic acid, which encodes to a protein, which activated the BMP signaling pathway. In another embodiment, the protein, which activated the BMP signaling pathway, is a member of the BMP family. In another embodiment, the BMP is a BMP2.

The term "protein which activates BMP mediated signaling pathway" is defined hereinabove as a protein that can activate the BMP receptors, or the signaling cascade down stream of the receptor to elicit BMP specific cellular response. Examples, without being limited are members of the BMP family, such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076, and 5,141,905; BMP-8, disclosed in PCT publication WO91/18098; BMP-9, disclosed in PCT publication WO93/00432; and BMP-10 or BMP-11, disclosed in co-pending patent application Ser. No. 08/061,695 presently abandoned, a continuation-in-part of which has issued as U.S. Pat. No. 5,637,480, and Ser. No. 08/061,464 presently abandoned, a continuation-in-part of which has issued as U.S. Pat. No. 5,639,638 filed on May 12, 1993. Other agents, which interact with SMAD, can be for example, without limitation DPC4 (G. Lagna et al., "Partnership Between DPC4 and Smad Proteins in TGF-beta Signaling Pathways," Nature 383:832-836, 1996).

The engineered cells or tissue of the invention of the invention may comprise, in addition to a tendon/ligament-inducing protein such as BMP-12 or VL-1 (BMP-13), other therapeutically useful agents including MP52, epidermal growth factor (EGF), fibroblast growth factor (FGF), platelet derived growth factor (PDGF), transforming growth factors (TGF-α and TGF-β), and fibroblast growth factor-4 (FGF-4), parathyroid hormone (PTH), leukemia inhibitory factor (LIF/HILDA/DIA), insulin-like growth factors (IGF-I and IGF-II). Portions of these agents may also be used in compositions of the present invention. Such a composition may be useful for treating defects of the embryonic joint where tendon, ligaments, and bone form simultaneously at contiguous anatomical locations, and may be useful for regenerating tissue at the site of tendon attachment to bone. It is contemplated that the compositions of the invention may also be used in wound healing, such as skin healing and related tissue repair. The types of wounds include, but are not limited to burns, incisions and ulcers.

The vector may include in one embodiment a nucleic acid which codes for a fusion proteins. Fusion proteins can be purified by affinity chromatography using reagents that bind to the fusion partner. The reagent can be a specific ligand of the fusion partner or an antibody, preferably a monoclonal antibody. For example, fusion proteins containing beta-galactosidase can be purified by affinity chromatography using an anti-beta-galactosidase antibody column (Ullman 1984). Similarly, fusion proteins containing maltose binding protein can be purified by affinity chromatography using a column containing cross-linked amylose; see Guan, European Patent Application 286,239.

Optionally, the DNA that encodes the fusion protein is engineered so that the fusion protein contains a cleavable site between the protein and the fusion partner. The protein can occur at the amino-terminal or the carboxy-terminal side of the cleavage site. Both chemical and enzymatic cleavable sites are known in the art. Suitable examples of sites that are cleavable enzymaticaily include sites that are specifically recognized and cleaved by collagenase (Keil et al. 1975); enterokinase (Hopp et al. 1988); factor Xa (Nagai et al. 1987); and thrombin (Eaton et al. 1986). Collagenase cleaves between proline and X in the sequence Pro-X-Gly-Pro (SEQ ID NO:23) wherein X is a neutral amino acid. Enterokinase cleaves after lysine in the sequence Asp-Asp-Asp-Asp-Lys (SEQ ID NO:22). Factor Xa cleaves after arginine in the sequence Ile-Glu-Gly-Arg (SEQ ID NO:24). Thrombin cleaves between arginine and glycine in the sequence Arg-Gly-Ser-Pro (SEQ ID NO:25).

The skilled artisan appreciates that, if an amino acid sequence (primary structure) is known, a family of nucleic acids can then be constructed, each having a sequence that differs from the others by at least one nucleotide, but where each different nucleic acid still encodes the same protein. For example, if a protein has been sequenced but its corresponding gene has not been identified, the gene can be acquired through amplification of genomic DNA using a set of degenerate primers that specify all possible sequences encoding the protein.

The protein encoded by the nucleic acid of the invention, and functional analogs of the encoded protein, are essentially pure. For the purposes of this specification, "essentially pure" means that the protein and functional analogs are free from all but trace amounts of other proteins as well as of materials used during the purification process. A protein is considered to be essentially pure if it is at least 85%, preferably at least 90%, and more preferably at least 95% pure. Methods for purifying proteins are known in the art.

Determination of whether two amino acid sequences are substantially homologous is, for the purpose of the present specification, based on FASTA searches in accordance with Pearson et al. (1988). In the present specification, the amino acid sequence of a first protein is considered to be homologous to that of a second protein if the amino acid sequence of the first protein has at least about 20% amino acid sequence identity, preferably at least about 40% identity, and more preferably at least about 60% identity, with the sequence of the second protein. In the case of proteins having high homology, the amino acid sequence of the first protein has at least about 75% sequence identity, preferably at least about 85% identity, and more preferably at least about 95% identity, with the amino acid sequence of the second protein.

The protein encoded by the nucleic acid of the present invention further includes functional homologs. A protein is considered a functional homologue of another protein for a specific function, as described below, if the homologue has the same function as the other protein. The homologue can be, for example, a fragment of the protein, or a substitution, addition, or deletion mutant of the protein.

As is also known, it is possible to substitute amino acids in a sequence with equivalent amino acids. Groups of amino acids known normally to be equivalent are:
  (a) Ala(A), Ser(S), Thr(T), Pro(P), Gly(G);
  (b) Asn(N), Asp(D), Glu(E), Gln(Q);
  (c) His(H), Arg(R), Lys(K);
  (d) Met(M), Leu(L), Ile(I), Val(V); and
  (e) Phe(F), Tyr(Y), Trp(W).

Substitutions, additions, and/or deletions in the amino acid sequences can be made as long as the protein encoded by the nucleic acid of the invention continues to satisfy the functional criteria described herein. An amino acid sequence that is substantially the same as another sequence, but that differs from the other sequence by means of one or more substitutions, additions, and/or deletions, is considered to be an equivalent sequence. In one embodiment, less than 50%, in another embodiment less than 25%, and in another embodiment, less than 10%, of the number of amino acid residues in a sequence are substituted for, added to, or deleted from the protein encoded by the nucleic acid of the invention.

Other specific mutations of the sequences of the proteins of the invention described herein may involve modifications of a glycosylation site. These modifications may involve O-linked or N-linked glycosylation sites. For instance, the absence of glycosylation or only partial glycosylation at the asparagine-linked glycosylation sites results from amino acid substitution or deletion at the asparagine-linked glycosylation recognition sites.

The recombinant protein is purified by methods known in the art. Such methods include affinity chromatography using specific antibodies. Alternatively, the recombinant protein can be purified using a combination of ion-exchange, size-exclusion, and hydrophobic interaction chromatography using methods known in the art. These and other suitable methods are described, e.g., in Marston (1987).

Mixtures of proteins can be separated by, for example, SDS-PAGE in accordance with the method of Laemmli (1970). The molecular weights were determined by resolving single bands on SDS-PAGE and comparing their positions to those of known standards. The method is understood by those in the art to be accurate within a range of 3-5%. Molecular weights can vary slightly between determinations.

The preparation and formulation of such pharmaceutically/physiologically acceptable compositions, having due regard to pH, isotonicity, stability and the like, is within the skill of the art. Methods of administration include topically, systemically, or locally as an injectable and/or implant or device. When administered, the composition for use in this invention is, of course, in a pyrogen-free, physiologically acceptable form. Further, the composition, may desirably be encapsulated or injected in a viscous form for delivery to the site of tissue damage. Topical administration may be suitable for wound healing and tissue repair. Therapeutically useful agents other than the proteins which may also optionally be included in the composition as described above, may alternatively or additionally, be administered simultaneously or sequentially with the composition in the methods of the invention.

In addition, the compositions of the present invention may be used in conjunction with presently available treatments for tendon/ligament injuries, such as suture (e.g., vicryl sutures or surgical gut sutures, Ethicon Inc., Somerville, N.J.) or tendon/ligament allograft or autograft, in order to enhance or accelerate the healing potential of the suture or graft. For example, the suture, allograft or autograft may be soaked in the compositions of the present invention prior to implantation. It may also be possible to incorporate the protein or composition of the invention onto suture materials, for example, by freeze-drying.

The compositions may be in a carrier such as an appropriate matrix and/or sequestering agent. For instance, the matrix may support the composition or provide a surface for tendon/ligament-like tissue formation and/or other tissue formation. The matrix may provide slow release of the protein and/or the appropriate environment for presentation thereof. The sequestering agent may be a substance which aids in ease of administration through injection or other means" or may slow the migration of protein from the site of application.

The choice of a carrier material is based on biocompatibility, biodegradability, mechanical properties, cosmetic appearance and interface properties. The particular application of the compositions will define the appropriate formulation. Potential matrices for the compositions may be biodegradable and chemically defined. Further matrices are comprised of pure proteins or extracellular matrix components. Other potential matrices are nonbiodegradable and chemically defined. Preferred matrices include collagen-based materials, including sponges, such as Helistat® (Integra LifeSciences, Plainsboro, N.J.), or collagen in an injectable form, as well as sequestering agents, which may be biodegradable, for example hyalouronic acid derived. Biodegradable materials, such as cellulose films, or surgical meshes, may also serve as matrices. Such materials could be sutured into an injury site, or wrapped around the tendon/ligament.

Another preferred class of carrier are polymeric matrices, including polymers of poly(lactic acid), poly(glycolic acid) and copolymers of lactic acid and glycolic acid. These matrices may be in the form of a sponge, or in the form of porous particles, and may also include a sequestering agent. Suitable polymer matrices are described, for example, in WO93/00050, the disclosure of which is incorporated herein by reference.

Preferred families of sequestering agents include blood, fibrin clot and/or cellulosic materials such as allcylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly (ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the activity of the progenitor cells.

Additional optional components useful in the practice of the subject application include, e.g. cryogenic protectors such as mannitol, sucrose, lactose, glucose, or glycine (to protect the protein from degradation during lyophilization), antimicrobial preservatives such as methyl and propyl parabens and benzyl alcohol; antioxidants such as EDTA, citrate and BHT (butylated hydroxytoluene); and surfactants sifdch as poly(sorbates) and poly(oxyethylenes); etc.

EXAMPLES

Experimental Procedures

DNA Constructs, Cell Culture and DNA Transfection

Murine SMAD 5 was cloned by RT-PCR with RNA isolated from the murine mesenchymal stem cell line C3H10T1/2 using the primers SMAD 5-FLAGfw (SEQ ID NO:15) and SMAD 5 rev (SEQ ID NO: 16). Rat SMAD-8 was isolated by RT-PCR with RNA isolated from rat brain (5 days old) using the primers SMAD-8 FLAG-fw (SEQ ID NO: 18) and SMAD-8 rev (SEQ ID NO: 19). Unique Bam HI and Sal I sites in forward and reverse primer-sequences allowed the directional integration in expression vector pMT7T3. SMAD and SMAD -variant expression are in this vector under the control of the LTR of the myeloproliferative virus (Ahrens et al., 1993). With a similar strategy SMAD 5 and SMAD-8-variants consisting of the linker and MH2 domain (L+MH2) were constructed by PCR from full-length SMAD clones using primer pairs SMAD5 L+MH2fw/SMAD 5rev (SEQ ID NOs:17 and 16) and SMAD-8 L+MH2fw/SMAD-8 rev (SEQ ID NOs:20 and 19), respectively. The integrity of the constructs was confirmed by sequencing. FLAG-tags were amino-terminally added to full-length SMAD s and their variants since forward primers used encode the respective peptide sequence (SEQ ID NO: 21). Murine C3H10T1/2 cells were routinely cultured in, tissue culture flasks in Dulbecco's modified Eagle's medium supplemented with 10% heat-inactivated FCS, 2 mM L-glutamine, and antibiotics (50 units/ml penicillin, 50 mg/ml streptomycin). Cells were transfected using FUGENE6 according to the manufacturer's protocol (Roche Diagnostics, Mannheim, Germany). C3H10T½ cells which recombinantly express BMP2 (C3H10T1/2-BMP2) cells were obtained by cotransfection with pSV2pac followed by selection with puromycine (5 µg/ml). Stable expression of the SMAD proteins and their variants in the C3H10T1/2-BMP2 background was done by cotransfection with pAG60, conferring resistance to G418 (750 µg/ml). Individual clones were picked, propagated, and tested for recombinant expression by RT-PCR (see below). Selected cell clones were subcultivated in the presence of puromycine or puromycme/G418 and the selective pressure was maintained during subsequent manipulations. The features of C3H10T1/2-BMP2 cells have been described (Ahrens et al., 1993; Hollnagel et al., 1997; Bchner et al., 1998). For the assessment of in vitro osteo-/chondrogenic development, cells were plated at a density of 5-7.5 ×10³ cells/cm². After reaching confluence (arbitrarily termed day 0) ascorbic acid (50 µg/ml) and 10 mM-glycerophosphate were added as specified by Owen et al., 1990.

RNA Preparation and RT-PCR

Total cellular RNAs were prepared by TriReagent$^{LS}$ according to the manufacturer's protocol (Molecular Research Center Inc.). Five µg of total RNA was reverse transcribed and cDNA aliquots were subjected to PCR. RT-PCR was normalized by the transcriptional levels of HPRT.

Western Blotting

Recombinant cells from petri dishes (13.6 cm diameter) were harvested at different time points at (day 0) and after (days 4, 7) confluence. Lysis was in RIPA buffer (1% (v/v) nonidet P-40, 0.1% SDS (w/v), 0.5% sodium deoxycholate in PBS, containing 100 µg/ml PMSF, 2 µg/ml aprotinin, and 1 mM $Na_3VO_4$). Lysates were centrifuged (30 min, 10.000 g, 4° C.) and the supernatants were stored at −70° C. until analysis. Protein concentration of the lysates was determined using coomassie brilliant blue. Protein was precipitated with ethanol, resuspended in reducing (containing DTT) and subjected to SDS-gel electrophoresis in 12.5%T polyacrylamide gels (20 µg/lane). Proteins were transferred to nitrocellulose membranes by semidry-blotting. Protein transfer was checked by staining of the membranes with Ponceau S. After blocking, membranes were incubated overnight at 4° C. with a monclonal antibody to the FLAG-tag (M2, F-3165, Sigma Chemical Co., St. Louis, Mo.). The secondary antibody (goat anti-mouse, horseradish peroxidase-conjugated; Dianova, Hamburg, Germany) was applied for 2 h at room temperature. Positive reactions were visualized with a chemiluminescence kit according to the manufactlrer's advice (Roche Diagnostics, Mannheim, Germany).

Histological Methods and Verification of Cellular Phenotypes

Osteoblasts exhibit stellate morphology displaying high levels of alkaline phosphatase which was visualized by cellular staining with SIGMA FAST BCIP/NBT (Sigma, St. Louis, Mo.).

In Vivo Transplantation

Figure 10:
FIG. 10: An electron microscope image of the ligament formed after SMAD 8/BMP2 cells injection.

Before in vivo transplantation, aliquots of 5×10⁶ cells in suspension (300? l) were prepared and injected subcutaneously in the scaral region of female C3H/HeN mice (4-8 weeks old). Before transplantation animals were anaesthetized with ketamine-xylazine mixture 30 µl/per mouse i.p. and injected i.p. with 5 mg/mouse of Cefamzolin (Cefamezin®, TEVA). Skin was swabbed with chlorhexidine gluconate 0.5%. For the detection of engrafted C3H10T1/2 cells the mice were sacrificed 10, 20 and 30 days after transplantation. Operated transplants were fixed in 4% paraformaldehyde cryoprotected with 5% sucrose overnight, embedded, and frozen. Sections were prepared with a cryostat (Bright, model OTF) and stained with H&E. FIG. 10 is an electron microscope image of the harvested tissue. FIG. 10 shows an electron microscope image of the ligament formed after SMAD-8/BMP2 cells injection. This image shows packed bundles of collagen in the implant, which is characteristic of ligament tissue. Very few collagen bundles were formed in the control transplant on the left.

EXPERIMENTAL RESULTS

Example 1

Cloning of SMAD-8 Protein from Rat Brain and SMAD 5 from C3H10T1/2 Cells

The SMAD-8 cDNA was cloned from rat brain (5 days old) by RT-PCR (FIG. 1, shaded). The forward primer contained sequences encoding a FLAG-tag allowing the detection of SMAD-8 with anti-FLAG antibodies (ABs). In front of the startcodon ATG is a consensus Kozak-sequence (FIG. 1, bold letters) allowing efficient translational initiation. Similarly, the SMAD-8 variant consisting of the linker and of the MH2-domain (SMAD-8 L+MH2) were constructed. The protein sequences with the aminoterminal FLAG-tags (shaded) are given in FIG. 2. By a similar cloning strategy SMAD 5 and SMAD 5 L+MH2 were cloned from RNA isolated from C3H10T1/2 cells (Methods Section).

Figure 3B:
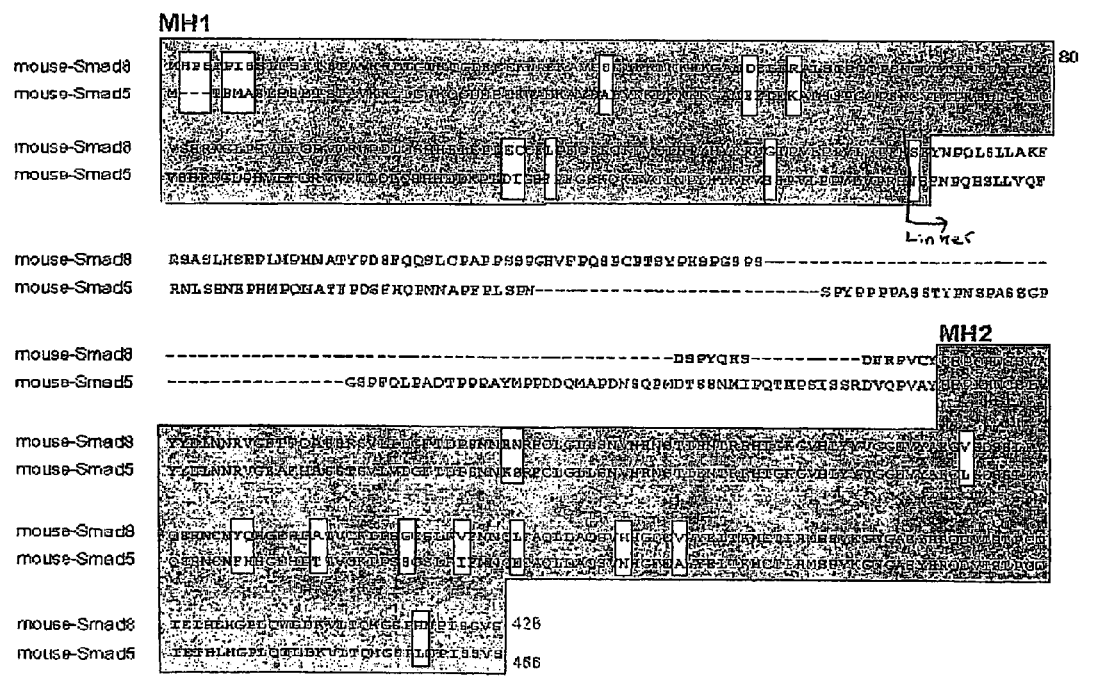

Unique restriction sites (Bam HI and Sal I) in forward and reverse primer-sequences allowed the directional integration in expression vector pMT7T3. SMAD and SMAD-variant expression are in this vector under the control of the LTR of the myeloproliferative virus (Ahrens et al., 1993). The integrity of the constructs was confirmed by sequencing. A sequence comparison of rat and mouse SMAD-8 shows a high sequence identity: In the amino terminal MH1 domain two amino acid exchanges are monitored, two in the linker region while two amino acids are deleted in the mouse SMAD-8-linker domain. In the carboxy terminal SMAD-8 MH2 domain just one exchange is monitored (FIG. 3A). Although, MH1 and MH2 domain are highly conserved between SMAD 5 and SMAD-8, a higher level of amino acid exchanges may indicate functional differences between SMAD 5 and SMAD-8 (FIG. 3B). In the linker region only a very reduced level of identity is observed (FIG. 3B).

Example 2

Establishment of MSCs Lines Expressing SMAD-8 $^{WT}$, SMAD 5$^{WT}$ and SMAD-8 SMAD 5-Variants L+MH2

Murine C3H10T1/2 mesenchymal stem cells were transfected using FUGENE6 (Roche Diagnostics, Mannheim, Germany). C3H10T1/2 cells which recombinantly express BMP2 (C3H10T1/2-BMP2) cells were obtained by cotransfection with pSV2pac followed by selection with puromycine (5 μg/ml). Stable expression of the SMAD proteins and their variants in the C3H10T1/2-BMP2 background was done by cotransfection with pAG60, conferring resistance to G418 (750 μg/ml). Individual clones were picked, propagated, and tested for recombinant expression by RT-PCR. About 10 individual cellular clones were picked and tested for expression of recombinant SMAD proteins by RT-PCR. Clones which express a high level of the transgene were propagated further and frozen. Selected cell clones were subcultivated in the presence of puromycine or puromycine/G418 and the selective pressure was maintained during subsequent manipulations. The features of C3H10T1/2-BMP2 cells have been described (Ahrens et al., 1993; Hollnagel et al., 1997; Buchner et al., 1998. For the assessment of in vitro osteo-/chondrogenic development, cells were plated at a density of 5-7.5×10³ cells/cm². After reaching confluence (arbitrarily termed day 0) ascorbic acid (50 μg/ml) and 10 mM—glycerophosphate were added as specified by Owen et al., 1990.

Example 3

Recombinant Expression of SMAD s in C3H10T1/2-BMP2

Figure 4:
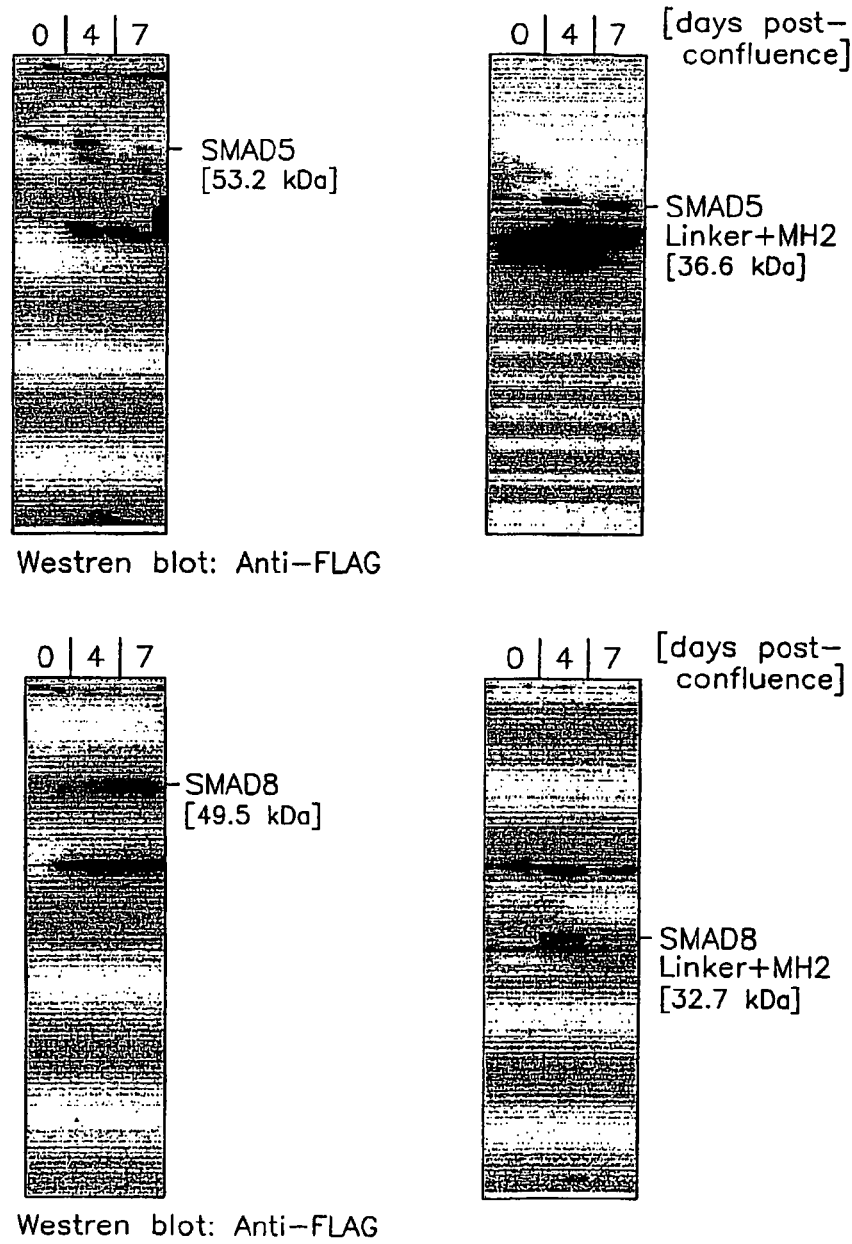
FIG. 4. Western immunoblotting which show recombinant expression of FLAG-tagged SMAD 5 and SMAD 8 variants in C3H10T1/2-BMP2.

The level of SMAD-expression in C3H10T1/2-BMP2 was investigated by immunoblotting cellular extracts at day 0, 4, and 7 post-confluence. Confluence has arbitrarily been termed day 0. Western blotting and immuno-detection of FLAG-tagged SMAD s was as described in the Methods Section. In cellular extracts of C3H10T1/2-BMP2 the expression of SMAD-8 $^{WT}$ and SMAD 5$^{WT}$ can easily be monitored (FIG. 4). Also FlLAG-tagged SMAD-8 PROTEIN L+MH2 and SMAD 5 L+MH2 domains are detectable and correspond to the expected size (FIG. 4).

Example 4

Biological Characterisation of SMAD-8 and SMAD 5-Expressing MSCs In Vitro

Forced expression of SMAD 5$^{WT}$ enhances osteogenic differentiation in mesenchymal progenitors which express recombinant BMP2 (C3H10T1/2-BMP2/SMAD 5) (FIG. 5). This is highlighted by enhanced levels of alkaline phosphatase positive cells in C3H10T1/2-BMP2 cells which express recombinant SMAD 5$^{WT}$ in comparison with parental C3H10T1/2-BMP2 cells alone. Also, osteocalcin and PTH/PTHrP receptor expression in C3H10T1/2-BMP2/SMAD 5 cells is enhanced in comparison with C3H10T1/2-BMP2 cells (FIG. 7). In contrast, SMAD-8 $^{WT}$ expression in C3H10T1/2-BMP-cells does not lead to enhanced levels of alkaline phosphatase synthesis (FIG. 5). This may indicate that BMP2 seems ineffective to mediate efficient activation of SMAD-8 in C3H10T1/2.

It has been demonstrated that SMAD domains consisting of the M12 domain or L+MH2 domain exert constitutive biological activity (Liu et al., 1996; Baker and Harland, 1996; Meersseman et al., 1997; Ju et al., 2000). Indeed, SMAD 5 L+MH2 domain expression in C3H10T1/2-BMP2 leads to higher levels of osteocalcin and PTH/PTHrP receptor synthesis. Interestingly, in contrast to SMAD-8 $^{WT}$, the biological active SMAD-8 L+MH2 domain gives rise to enhanced levels of alkaline phosphatase positive cells and to enhanced levels of osteocalcin synthesis in C3H10T1/2-BMP2 cells (FIGS. 5, 6). These cells, however, exhibit a completely different phenotype in comparison with C3H10T1/2-BMP2 cells. They display a lengthy morphology and do not exhibit the stellate structured phenotype of osteoblastic cells (C3H10T1/2-BMP2) (FIG. 8). C3H10T1/2-BMP2/SMAD-8 L+M12 cells are reminscent of ligament/tendon forming tendocytes. Indeed, C3H10T1/2-BMP2/SMAD-8 L+MH2 cells exhibit significant higher expression levels of Six1 expression than in parental C3H10T1/2-BMP2 cells. Six1 and Six2 are marker genes for ligament formation (Oliver et al., 1995). Six2 is not expressed in these cells on the basis of RT-PCR experiments. Also elastin expression could not demonstrated by RT-PCR. However, since only one set of primers pairs were used for RT-PCR in both cases, these experiments should be redone with other primer pairs.

Example 5

Biological Characterization of SMAD-8 PROTEIN-Expressing MSCs In Vivo

Figure 9C:
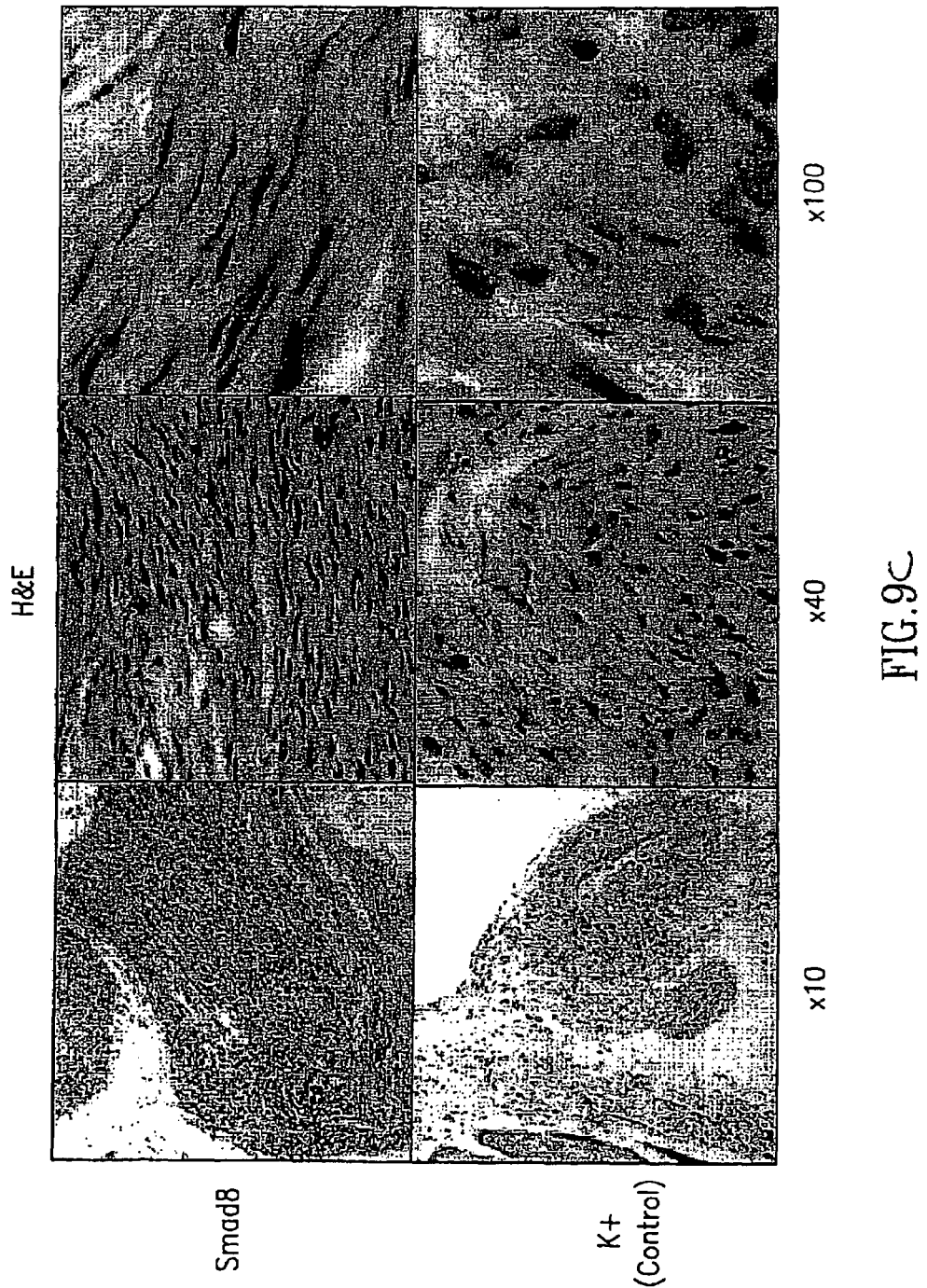

5×10⁶ of C3H10T1/2-BMP2/SMAD-8 L+MH2 cells were injected (300 μl) ectopically into the sacral subcutan tissue of female C3H/HeN mice (4-8 weeks old). Thirty days after transplantation a mass of semi soft tissue was formed in the transplantation site which was shown to be a large mass of spindle shaped tendocytes, as was shown by Histology (FIG. 9). In comparison, in transplants of wild type C3H10T1/2 only a mass of un-specific connective tissue was formed. These results demonstrate that SMAD-8 expression in MSCs leads in vivo to the formation of tendocytes.

Example 6

Genetic Engineering of Human Adult Mesenchymal Stem Cells to Express the SMAD-8 Gene:

Cells Isolation:

Human Adult Mesenchymal Stem Cells (hAMSCs) were isolated from explants of human bone marrow surgical waste and expanded in vitro. Isolation of hMSCs was performed as follows: 10 ml marrow aspirates were collected into a tube with 6000 U heparin, washed with PBS, and recovered cells were collected by centrifugation at 900 g. Collected cells were then loaded onto Percoll solution (density 1.073 g/ml). Cell separation was accomplished by centrifugation at 1100 g (30 min at 20° C.). Nucleated cells collected were washed twice with PBS and then cultured in 1010 nm culture plates.

Tissue Culture:

Cells were cultured in low glucose, low bicarbonate DMEM medium (Beit Haemek)+10% fetal calf serum (Beit Haemek), the environmental conditions were of 5% CO2 and 37° C.

Cells transfection:

$3\times10^6$ hAMSCs were transfected with 30 ug of the SMAD-8 plasmid using the Amaxa Nucleofector™ technology and in accordance with the manufacturer's preliminary protocol for hAMSCs. Briefly, the harvested cells were aliquoted in $5\times10^5$ cells, recovered by centrifugation, and resuspended in 100 μl of Amaxa's nucleofection solution. Five micrograms of DNA plasmid were added to the suspended cells, mixed well and transferred to electroporation cuvette, provided by the Amaxa nucleofection kit. The electroporation was performed using the G22 program, that was proven to be optimal for the transfection of hAMSCs. Immediately after the electroporation, the cells were transferred into 6-well plates, containing 4 ml complete growth medium equilibrated to 37° C., 5% CO2, and incubated at 37° C. in 5% $CO_2$ atmosphere for 24 hours. The same procedure was performed using 2.5 ug of SMAD-8 plasmid and 2.5 ug of rhBMP2 plasmid in order to achieve simultaneous over expression of both genes in the cells.

Detection of Gene Expression:

5, 10 and 15 days post transfection, RNA was isolated from the cells using the Trizol reagent and protocol provided by the manufacturer (Life Sciences). 2 ug of RNA were transformed into cDNA by Reverse Transcriptase (RT) reaction. PCR was then performed using specific primers to the SMAD-8 cDNA. 20 ul of the PCR reaction sample were loaded into a 2% Agarose gel stained with Etidium Bromide. The gel analysis demonstrated a band matching the expected amplified region in the SMAD-8 cDNA (see FIG. 11).

Example 7

SMAD8/BMP2 Cells' Implantation in a Tendon Defect Model:

Experimental Procedures

Cell culture: SMAD8/BMP2 cells were cultured as described above.

Cell labeling: Prior to implantation, cells were trypsinized, centrifuged for 5 minutes in 1200 RPM, and resuspended in 6 ml serum free medium. The cells were counted and labeled with 10 ul of DiI fluorescent dye. After 25 minutes of incubation in 37° C. degrees, the cells were centrifuged, washed in serum free medium and $1.5\times10^6$ labeled cells were seeded on a 3×3×1 mm Collagen I matrix (Duragen).

Figure 12:
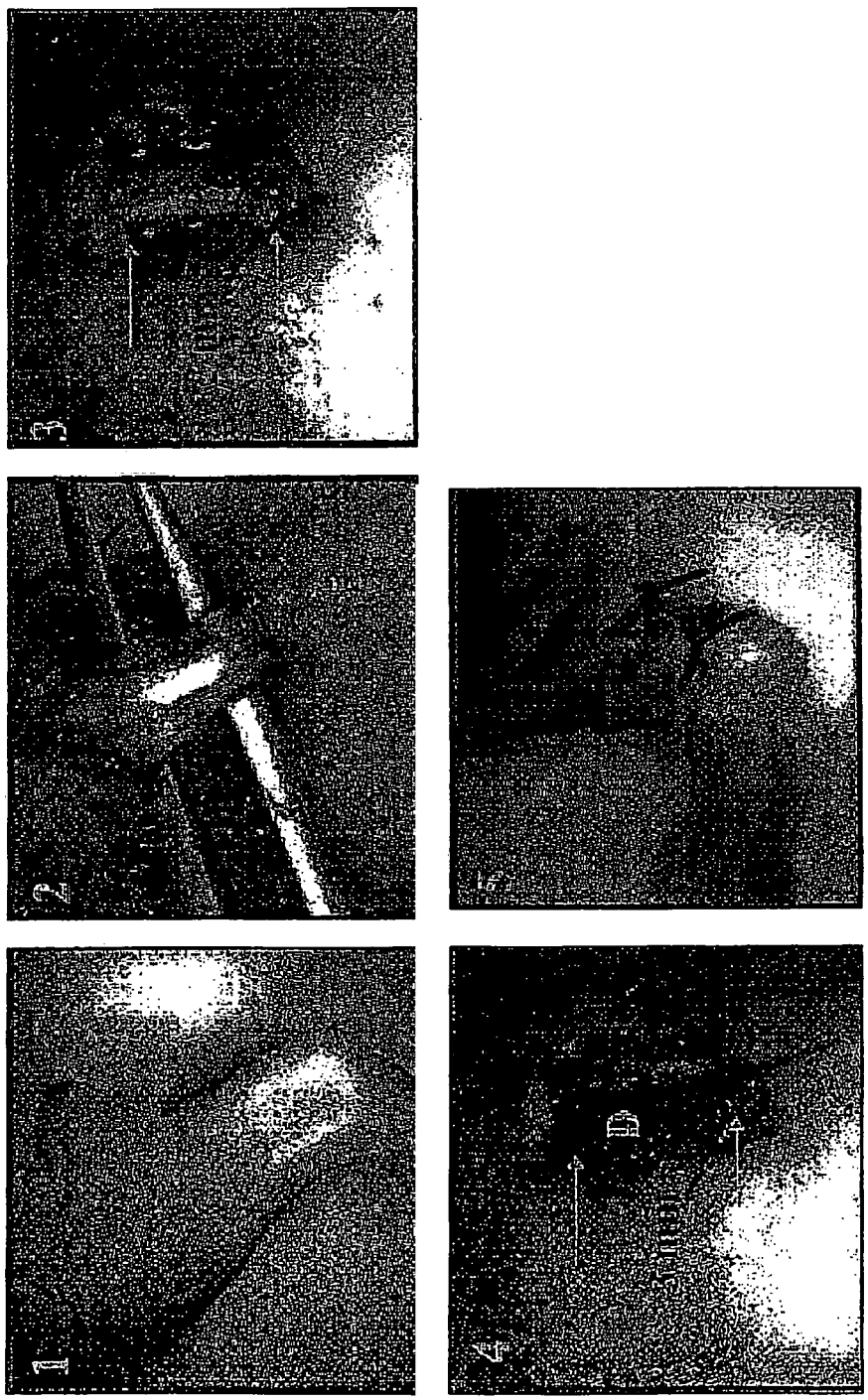
FIG. 12: Demonstrates an induced non regenerating Achilles tendon injury model.

Injury model: Achilles tendon gap model in athymic rat- Adult athymic rats (4 months old) were anaesthetized with Ketamine-Xylazine mixture (75 mg/kg Ketamine and 10 mg/kg Xylazine injected i.p.). In addition to that rats were injected with Rimadyl 5 mg/kg, i.p. in order to reduce postoperative pain and inflammatory response. Skin was shaved and swabbed with chlorhexidine gluconate 0.5%. The gastrocnemius tendon the athymic rat was separated from plantaris and soleus tendons and 3 mm long partial resection defect will be created in the lateral substance of the gustrocnemius tendon (FIG. 12). Implants were placed into the created defect, and sutured to the tendon with 6/0 Polypropylene monofilament non-absorbable suture. Skin was closed in a routine manner using 2/0 Mersilk. The tension on the tendon was returned to approximately normal. The rats were allowed to move immediately postoperatively in their cages.

Detection of the SMAD8/BMP2 cells in the injury site: 4 weeks post implantation the rats were sacrificed using $CO_2$. The Achilles tendon was excised and fixed in 4% Paraformaldehyde for 40 minutes and then suspended in 2M Sucrose over night. The sample were embedded in OCT, frozen in liquid nitrogen. 10 um sections were made on Super frost slides. Sections were analyzed using confocal microscope. Labeled cells were found within the implantation area, adjacent to the tendon tissue (FIG. 13), indicating cell survival and engraftment within the injury site. Additional samples were fixed in 4% Formalin over night and processed for Histology. Samples were embedded in paraffin and 5 um sections were made using a motorized microtome.

Experimental Results

Following hematoxilne-Eosine routine staining, a layer of tendon-like tissue was formed at the border of the implant (see FIG. 13).

What is claimed is:

1. A method of repairing a tendon or ligament injury or defect, the method comprising implanting at the site of the injury or defect an autologous engineered mesenchymal stem cell which comprises a nucleic acid sequence encoding BMP-2 and a nucleic acid sequence encoding a SMAD-8 protein comprising intact Linker region and MH2 domain (L+MH2) of SMAD-8, so as to induce repair of the tendon or ligament tissue.

2. The method of claim 1, wherein said mesenchymal stem cell is an adult mesenchymal stem cell.

3. The method of claim 1, wherein said mesenchymal stem cell further expresses one or more proteins which activate the BMP signaling pathway.

4. A method of regenerating tendon or ligament tissue the method comprising contacting a tendon or ligament tissue and/or implanting said tendon or ligament tissue with an autologous engineered mesenchymal stem cell which comprises a nucleic acid sequence encoding BMP-2 and a nucleic acid sequence encoding a SMAD-8 protein comprising intact Linker region and MH2 domain (L+MH2) of SMAD-8, so as to regenerate the tendon or ligament tissue.

5. The method of claim 4, wherein said mesenchymal stem cell is an adult mesenchymal stem cell.

6. The method of claim 1, wherein said SMAD-8 protein comprises SEQ ID No.:2.

7. The method of claim 4, wherein said SMAD-8 protein comprises SEQ ID No.:2.

* * * * *

SEQUENCE LISTING

<160> NUMBER OF SEQ ID NOS: 2

<210> SEQ ID NO 1
<211> LENGTH: 283
<212> TYPE: PRT
<213> ORGANISM: Homo sapiens

<400> SEQUENCE: 1

Ser Glu Tyr Asn Pro Gln Leu Ser Leu Leu Ala Lys Phe Arg Ser Ala
1               5                   10                  15

Ser Leu His Ser Glu Pro Leu Met Pro His Asn Ala Thr Tyr Pro Asp
            20                  25                  30

Ser Phe Gln Gln Pro Pro Cys Ser Ala Leu Pro Pro Ser Pro Ser His
        35                  40                  45

Ala Phe Ser Gln Ser Pro Cys Thr Ala Ser Tyr Pro His Ser Pro Gly

```
                50                  55                  60
Ser Pro Ser Glu Pro Glu Ser Pro Tyr Gln His Ser Asp Phe Arg Pro
 65                  70                  75                  80

Val Cys Tyr Glu Glu Pro Gln His Trp Cys Ser Val Ala Tyr Tyr Glu
                 85                  90                  95

Leu Asn Asn Arg Val Gly Glu Thr Phe Gln Ala Ser Ser Arg Ser Val
                100                 105                 110

Leu Ile Asp Gly Phe Thr Asp Pro Ser Asn Asn Arg Asn Arg Phe Cys
                115                 120                 125

Leu Gly Leu Leu Ser Asn Val Asn Arg Asn Ser Thr Ile Glu Asn Thr
130                 135                 140

Arg Arg His Ile Gly Lys Gly Val His Leu Tyr Tyr Val Gly Gly Glu
145                 150                 155                 160

Val Tyr Ala Glu Cys Val Ser Asp Ser Ser Ile Phe Val Gln Ser Arg
                165                 170                 175

Asn Cys Asn Tyr Gln His Gly Phe His Pro Ala Thr Val Cys Lys Ile
                180                 185                 190

Pro Ser Gly Cys Ser Leu Lys Val Phe Asn Asn Gln Leu Phe Ala Gln
                195                 200                 205

Leu Leu Ala Gln Ser Val His His Gly Phe Glu Val Val Tyr Glu Leu
210                 215                 220

Thr Lys Met Cys Thr Ile Arg Met Ser Phe Val Lys Gly Trp Gly Ala
225                 230                 235                 240

Glu Tyr His Arg Gln Asp Val Thr Ser Thr Pro Cys Trp Ile Glu Ile
                245                 250                 255

His Leu His Gly Pro Leu Gln Trp Leu Asp Lys Val Leu Thr Gln Met
                260                 265                 270

Gly Ser Pro His Asn Pro Ile Ser Ser Val Ser
            275                 280

<210> SEQ ID NO 2
<211> LENGTH: 200
<212> TYPE: PRT
<213> ORGANISM: Homo sapiens

<400> SEQUENCE: 2

Glu Glu Pro Gln His Trp Cys Ser Val Ala Tyr Tyr Glu Leu Asn Asn
 1               5                  10                  15

Arg Val Gly Glu Thr Phe Gln Ala Ser Ser Arg Ser Val Leu Ile Asp
                20                  25                  30

Gly Phe Thr Asp Pro Ser Asn Asn Arg Asn Arg Phe Cys Leu Gly Leu
                35                  40                  45

Leu Ser Asn Val Asn Arg Asn Ser Thr Ile Glu Asn Thr Arg Arg His
 50                  55                  60

Ile Gly Lys Gly Val His Leu Tyr Tyr Val Gly Gly Glu Val Tyr Ala
 65                  70                  75                  80

Glu Cys Val Ser Asp Ser Ser Ile Phe Val Gln Ser Arg Asn Cys Asn
                85                  90                  95

Tyr Gln His Gly Phe His Pro Ala Thr Val Cys Lys Ile Pro Ser Gly
                100                 105                 110

Cys Ser Leu Lys Val Phe Asn Asn Gln Leu Phe Ala Gln Leu Leu Ala
                115                 120                 125

Gln Ser Val His His Gly Phe Glu Val Val Tyr Glu Leu Thr Lys Met
                130                 135                 140
```

-continued

```
Cys Thr Ile Arg Met Ser Phe Val Lys Gly Trp Gly Ala Glu Tyr His
145                 150                 155                 160

Arg Gln Asp Val Thr Ser Thr Pro Cys Trp Ile Glu Ile His Leu His
                165                 170                 175

Gly Pro Leu Gln Trp Leu Asp Lys Val Leu Thr Gln Met Gly Ser Pro
            180                 185                 190

His Asn Pro Ile Ser Ser Val Ser
        195                 200
```